(12) United States Patent
Vlodaver et al.

(10) Patent No.: US 9,700,684 B2
(45) Date of Patent: *Jul. 11, 2017

(54) MEDICAL DELIVERY DEVICES AND METHODS FOR APPLYING A BARRIER COMPOSITION TO A TARGETED SKIN SURFACE

(71) Applicant: Preventamedics LLC, Eden Prairie, MN (US)

(72) Inventors: Aner Vlodaver, Eden Prairie, MN (US); Benhoor Soumekh, Minnetonka, MN (US); Smarajit Mitra, West St. Paul, MN (US); Sumita B. Mitra, West St. Paul, MN (US)

(73) Assignee: Preventamedics LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/070,328

(22) Filed: Mar. 15, 2016

(65) Prior Publication Data

US 2016/0193431 A1 Jul. 7, 2016

Related U.S. Application Data

(63) Continuation of application No. 14/690,758, filed on Apr. 20, 2015, now Pat. No. 9,314,601, which is a
(Continued)

(51) Int. Cl.
| | | |
|---|---|---|
| *A01N 65/00* | (2009.01) | |
| *A61M 11/00* | (2006.01) | |
| *A61M 35/00* | (2006.01) | |
| *A01N 65/12* | (2009.01) | |
| *A01N 37/12* | (2006.01) | |
| *A01N 47/44* | (2006.01) | |
| *A01N 33/12* | (2006.01) | |
| *A01N 31/16* | (2006.01) | |
| *A01N 65/28* | (2009.01) | |
| *A01N 65/06* | (2009.01) | |
| *A01N 25/06* | (2006.01) | |
| *A01N 31/04* | (2006.01) | |
| *A01N 31/08* | (2006.01) | |
| *A01N 35/02* | (2006.01) | |
| *A01N 37/10* | (2006.01) | |
| *A01N 43/50* | (2006.01) | |
| *A01N 47/12* | (2006.01) | |
| *A01N 49/00* | (2006.01) | |
| *A01N 63/02* | (2006.01) | |
| *A01N 65/03* | (2009.01) | |
| *A01N 65/32* | (2009.01) | |
| *A01N 43/16* | (2006.01) | |
(Continued)

(52) U.S. Cl.
CPC ........ *A61M 11/001* (2014.02); *A01N 25/04* (2013.01); *A01N 25/06* (2013.01); *A01N 31/04* (2013.01); *A01N 31/08* (2013.01); *A01N 31/16* (2013.01); *A01N 33/12* (2013.01); *A01N 35/02* (2013.01); *A01N 37/10* (2013.01); *A01N 37/12* (2013.01); *A01N 43/16* (2013.01); *A01N 43/50* (2013.01); *A01N 47/12* (2013.01); *A01N 47/44* (2013.01); *A01N 49/00* (2013.01); *A01N 63/02* (2013.01); *A01N 65/03* (2013.01); *A01N 65/06* (2013.01); *A01N 65/08* (2013.01); *A01N 65/12* (2013.01); *A01N 65/28* (2013.01); *A01N 65/32* (2013.01); *A61K 8/046* (2013.01); *A61K 8/31* (2013.01); *A61K 8/345* (2013.01); *A61K 8/347* (2013.01); *A61K 8/375* (2013.01); *A61K 8/40* (2013.01); *A61K 8/416* (2013.01); *A61K 8/4946* (2013.01); *A61K 8/73* (2013.01); *A61K 8/922* (2013.01); *A61K 8/97* (2013.01); *A61K 9/0014* (2013.01); *A61K 9/06* (2013.01); *A61K 9/107* (2013.01); *A61K 9/12* (2013.01); *A61K 31/05* (2013.01); *A61K 31/14* (2013.01); *A61K 31/23* (2013.01); *A61K 31/4164* (2013.01); *A61K 31/721* (2013.01); *A61K 47/14* (2013.01); *A61K 47/44* (2013.01); *A61M 35/003* (2013.01); *A61M 35/006* (2013.01); *A61Q 17/005* (2013.01); *B05B 9/0838* (2013.01); *B65D 83/0038* (2013.01); *B65D 83/48* (2013.01); *B65D 83/64* (2013.01); *A01N 2300/00* (2013.01); *A61K 2800/87* (2013.01); *B65D 83/42* (2013.01)

(58) Field of Classification Search
CPC ...................................................... A61K 36/00
USPC ...................................................... 424/725
See application file for complete search history.

(56) References Cited

U.S. PATENT DOCUMENTS

| | | | |
|---|---|---|---|
| 7,754,449 | B2 | 7/2010 | Neefe et al. |
| 8,367,683 | B2 | 2/2013 | Herman |
(Continued)

FOREIGN PATENT DOCUMENTS

| | | |
|---|---|---|
| EP | 1059086 | 12/2000 |
| WO | WO 95/28136 | 10/1995 |
(Continued)

OTHER PUBLICATIONS

"HealMax Spray," Healmax-Agro Chem Inc., product brochure, available at www.healmaxspray.com, 2 pages (publicly available before Aug. 13, 2013).

Primary Examiner — Michael Meller
(74) Attorney, Agent, or Firm — Fish & Richardson P.C.

(57) ABSTRACT

Some embodiments of a system or method for applying a barrier composition to a targeted skin surface can be used to as a preventative measure to reduce the likelihood of trans-
(Continued)

mission of microbial entities from an external source (e.g., a floor surface or another surface) to the targeted skin surface.

19 Claims, 6 Drawing Sheets

Related U.S. Application Data continuation of application No. 13/965,745, filed on Aug. 13, 2013, now Pat. No. 9,028,884.

(51) Int. Cl.

| | | |
|---|---|---|
| *A01N 65/08* | (2009.01) | |
| *A61K 8/31* | (2006.01) | |
| *A61K 8/34* | (2006.01) | |
| *A61K 8/37* | (2006.01) | |
| *A61K 8/40* | (2006.01) | |
| *A61K 8/41* | (2006.01) | |
| *A61K 8/49* | (2006.01) | |
| *A61K 8/73* | (2006.01) | |
| *A61Q 17/00* | (2006.01) | |
| *A61K 8/92* | (2006.01) | |
| *A61K 8/97* | (2017.01) | |
| *A61K 8/04* | (2006.01) | |
| *A01N 25/04* | (2006.01) | |
| *A61K 31/05* | (2006.01) | |
| *A61K 31/14* | (2006.01) | |
| *A61K 31/23* | (2006.01) | |
| *A61K 31/4164* | (2006.01) | |
| *A61K 31/721* | (2006.01) | |
| *A61K 9/00* | (2006.01) | |
| *A61K 47/14* | (2017.01) | |
| *A61K 9/107* | (2006.01) | |
| *A61K 9/12* | (2006.01) | |
| *A61K 47/44* | (2017.01) | |
| *A61K 9/06* | (2006.01) | |
| *B05B 9/08* | (2006.01) | |
| *B65D 83/48* | (2006.01) | |
| *B65D 83/64* | (2006.01) | |
| *B65D 83/00* | (2006.01) | |
| *A61F 13/40* | (2006.01) | |
| *B65D 83/42* | (2006.01) | |

(56) References Cited

U.S. PATENT DOCUMENTS

| | | |
|---|---|---|
| 8,389,581 B2 | 3/2013 | DeMarco et al. |
| 2002/0110566 A1 | 8/2002 | Neefe et al. |
| 2008/0026039 A1* | 1/2008 | Popp .................... A61K 9/7023 424/443 |
| 2010/0093998 A1 | 4/2010 | Isobe et al. |
| 2010/0137451 A1 | 6/2010 | DeMarco et al. |
| 2013/0172425 A1 | 7/2013 | DeMarco et al. |

FOREIGN PATENT DOCUMENTS

| | | |
|---|---|---|
| WO | WO 97/42942 | 11/1997 |
| WO | WO 02/00242 | 1/2002 |
| WO | WO 2009/091976 | 7/2009 |
| WO | WO 2010/062961 | 6/2010 |

* cited by examiner

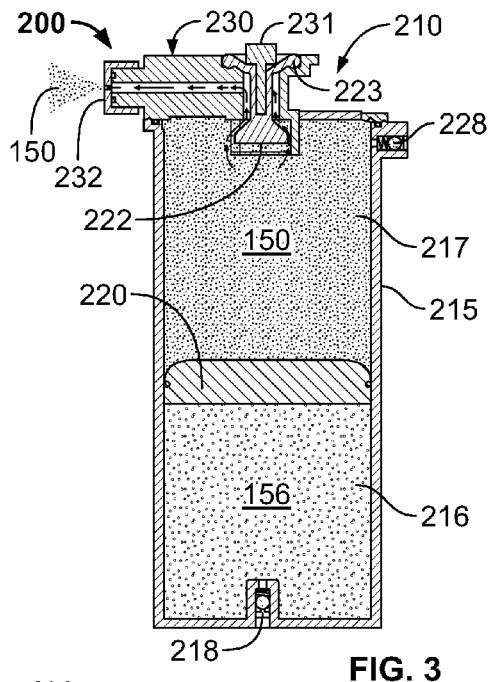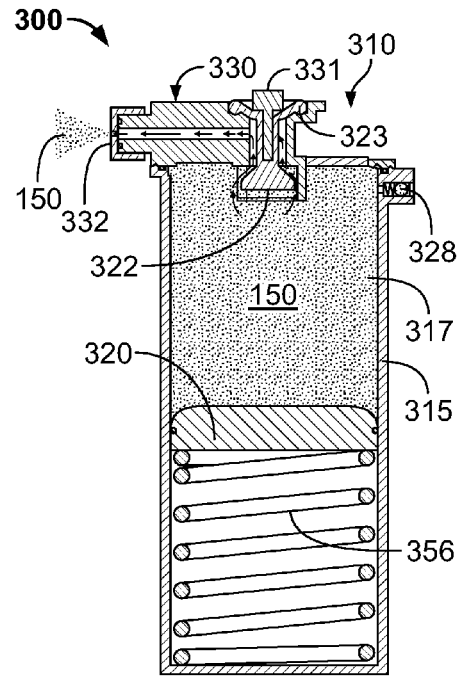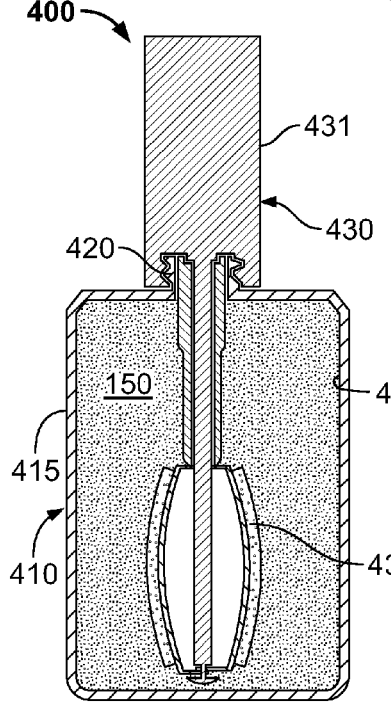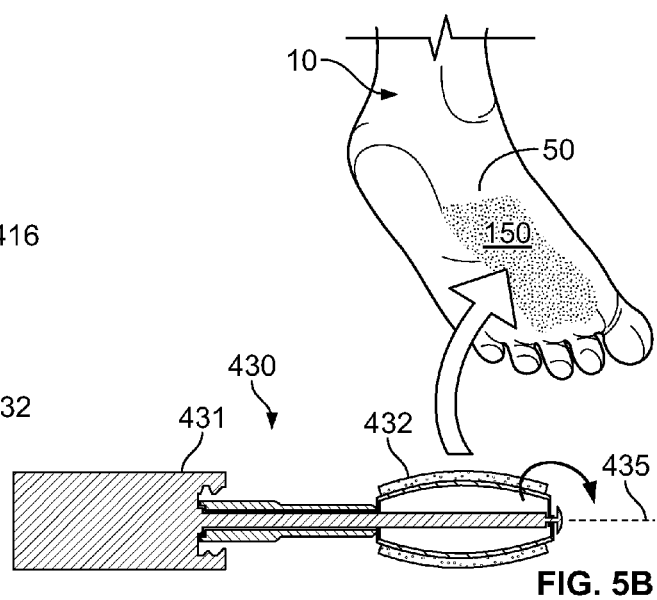
FIG. 3
FIG. 4
FIG. 5A
FIG. 5B

900

910
Mix Aqueous Phase Elements to Provide an Aqueous Phase Mixture

920
Mix Oil Phase Elements in Isolation from the Aqueous Phase Mixture to Provide an Oil Phase Mixture 930
Emulsify the Oil Phase Mixture in the Aqueous Phase Mixture by Rapid Agitation at a Selected Temperature Below 100 Degrees C so as to Provide a Wart-resistant Barrier Composition 940
Depositing the Wart-resistant Barrier Composition into a Reservoir of a Topical Skin Applicator Device

FIG. 9

MEDICAL DELIVERY DEVICES AND METHODS FOR APPLYING A BARRIER COMPOSITION TO A TARGETED SKIN SURFACE

CROSS-REFERENCE TO RELATED APPLICATIONS

This application is a continuation of U.S. application Ser. No. 14/690,758, filed Apr. 20, 2015, which is a continuation application of U.S. application Ser. No. 13/965,745, filed Aug. 13, 2013, which are incorporated herein by reference in their entirety.

TECHNICAL FIELD

This disclosure relates to medical delivery devices and methods for applying a barrier composition to a targeted skin surface, and also relates to compositions for use in such medical delivery devices and methods.

BACKGROUND

Some people suffer from the appearance of warts on portions of their skin, such as plantar warts that commonly develop on the bottom of people's feet. Such warts are typically caused by the human papillomavirus (HPV) occurring on the sole or toes of the foot. Plantar warts and other varieties of warts can be self-limiting, but a number of topical treatment options are available to treat the site of a plantar wart after the wart appears and grows on the skin. These skin warts are commonly caused when HPV spreads from a floor or other surface to infect a person via compromised skin through direct contact, for example, when HPV penetrates through the skin via tiny cuts and abrasions in the outermost layer of skin. After HPV infects the person, warts may not be visible or otherwise noticed for a period weeks. When such a wart appears, the wart can be painful if left untreated.

Presently, plantar warts are not prevented by inoculation (e.g., Gardasil, Cervarix, or the like) with currently available HPV vaccines because such warts are usually caused by different strains of HPV. Instead of using medical applications to prevent plantar warts on human skin, such warts are most commonly treated only after the warts appear on the infected skin. For example, typical post-infection treatments might include one or more of topical application of a salicylic acid product directly over the wart and repeated over a period of weeks, cryosurgery or other tissue destroying techniques, and surgical excision. In some circumstances, these treatment options can be painful, costly, time-consuming (including the recovery period), or a combination thereof, and furthermore such treatments may lead to scar formation.

SUMMARY

Some embodiments of a system for applying a barrier composition to a targeted skin surface can be used as a preventative measure to reduce the likelihood of transmission of HPV or other microbial entities from an external source (e.g., a floor surface or another source) to the targeted skin surface. In some examples described herein, the system can include a medical delivery device configured to apply a microbial-resistant barrier layer to a relatively large region of skin, such as the bottoms of a person's feet, before common HPV exposure periods (e.g., when walking barefoot in a pool area, in a shower area, in a sauna area, in a locker room area, in a gym area, or any other surface on which a skin surface may be exposed to HPV or other microbial entities). For instance, in some embodiments, the system may include a topical spray applicator device that dispenses a microbial-resistant barrier composition so as to provide a substantially continuous barrier layer that hinders the transmission of HPV and other microbial entities from the external source to the targeted skin surface. In other embodiments described herein, the system may include medical delivery devices other than a spray applicator device. A number of examples described herein illustrate the barrier layer being formed on a targeted skin surface of a foot, but it should be understood from the description herein that the microbial-resistant barrier composition can be applied to other portions of the body (e.g., elbows, hands, fingers, arms, legs, knees, and others) that may be exposed to viruses causing skin warts or to other microbial entities.

In some embodiments, a medical delivery device is configured for dispensing a barrier composition to a targeted skin surface for purposes of preventing the infection of wart-causing viruses along the targeted skin surface. The device can include a topical spray applicator nozzle having an exit port. The device can also include a reservoir in fluid communication with the exit port of the topical spray applicator nozzle, and the reservoir contains a topical skin barrier composition. The topical skin barrier composition optionally comprises: from about 30% to about 90% by weight of the composition of a vehicle, from about 0.5% to about 5% by weight of the composition of a preservative, and from about 0.5% to about 5% by weight of the composition of an active virucidal or virostatic agent. Also, the device may include an actuator configured to selectively open a fluid flow path from the reservoir to the exit port of the topical spray applicator nozzle during dispensation of the topical skin barrier composition from the exit port.

Particular embodiments described herein include a medical delivery device for dispensing a barrier composition to a targeted skin surface. The device may include a container body defining a reservoir. The reservoir contains a topical skin barrier composition. The topical skin barrier composition optionally comprises from about 30% to about 90% by weight of the composition of a vehicle, from about 0.5% to about 5% by weight of the composition of a preservative, and from about 0.5% to about 5% by weight of the composition of an active agent. Furthermore, the topical skin barrier composition may be configured to form an anti-microbial barrier coating along a targeted skin surface in response to dispensation from the reservoir that hinders transmission of wart-causing microbial entities to the targeted skin surface. In some optional implementations, the container body is a component of a device selected from the group consisting of: a topical spray applicator, a roller applicator, and a disposable applicator pad.

Some embodiments described herein include a method of using topical skin barrier composition to form an anti-microbial barrier layer along a targeted skin surface. The method may include depositing a barrier composition to a targeted skin surface. The method may also include maintaining the barrier composition on the targeted skin surface until an anti-microbial barrier layer is formed over an exterior of the targeted skin surface. The method may further include contacting the barrier layer to a floor or other source susceptible to carrying HPV or other microbial entities. Also, the method may optionally include removing the barrier layer from the targeted skin surface.

Various embodiments described herein include a method of manufacturing a medical delivery device containing a barrier composition configured to form an anti-microbial barrier layer along a targeted skin surface. The method may include mixing aqueous phase elements of a topical skin barrier composition together to provide an aqueous phase mixture. The method may also include mixing oil phase elements of the topical skin barrier composition together to provide an oil phase mixture. The method may further include emulsifying the oil phase mixture and the aqueous phase mixture to provide the topical skin barrier composition. Optionally, the emulsifying step occurs an elevated temperature from about 30° to about 100° C. Also, the method may include depositing the topical skin barrier composition into a medical delivery device configured to apply the topical skin barrier composition to a targeted skin surface for forming an anti-microbial barrier layer along the targeted skin surface.

Some embodiments described herein include a composition for forming a microbial-resistant, topical skin barrier layer over an exterior of a targeted skin surface. The composition may include from about 30% to about 90% by weight of the composition of a vehicle. Also, the composition may include from about 0.5% to about 5% by weight of the composition of a preservative. The composition may further include from about 0.5% to about 5% by weight of the composition of an active agent.

These and other embodiments described herein may optionally provide one or more of the following benefits. First, some embodiments include a medical delivery device that can be carried and selectively activated by a user to dispense a barrier composition to a targeted skin surface. The barrier composition may provide a microbial prevention screen over the targeted skin surface that reduces the likelihood of transmission of HPV or other wart-causing microbial entities from a floor surface or other external source. Second, in some embodiment, the barrier composition dispensed from the medical delivery device may optionally contain one or more active agents to destroy or inhibit transmission of viruses (such as HPV) or other microbial entities. Accordingly, the barrier layer formed on the skin surface can provide both a physical barrier effect (for example, a barrier layer of sufficient thickness to physically prevent penetration of HPV or other microbial entities to the skin surface) and an anti-microbial effect (e.g., for example, an agent that destroys or otherwise reduces the population of HPV or other microbial entities). Third, some embodiments of the system dispense the barrier composition so as to provide a non-tacky, generally transparent coating along the skin surface that does not interfere with the user's normal actions (e.g., walking, swimming, etc.) when wearing the barrier layer. Fourth, in some methods of use described herein, the barrier layer formed along the skin surface can remain intact for an extended period of time during normal actions of the user, but can be readily removed by washing of the skin surface. Fifth, in some implementations, the barrier composition can be manufactured in an efficient process that also provides a prolonged, stable shelf life for the barrier composition after it is deposited into the medical delivery device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a cross-sectional view of another medical delivery device for applying a barrier composition to a targeted skin surface, in accordance with some embodiments.

FIG. 4 is a cross-sectional view of yet another medical delivery device for applying a barrier composition to a targeted skin surface, in accordance with some embodiments.

FIGS. 5A-B is a cross-sectional view of another medical delivery device for applying a barrier composition to a targeted skin surface, in accordance with some embodiments.

FIG. 9 is a chart of method for manufacturing a barrier composition and a medical delivery device for applying the barrier composition.

Like reference symbols in the various drawings indicate like elements.

DETAILED DESCRIPTION OF ILLUSTRATIVE EMBODIMENTS

Figure 1:
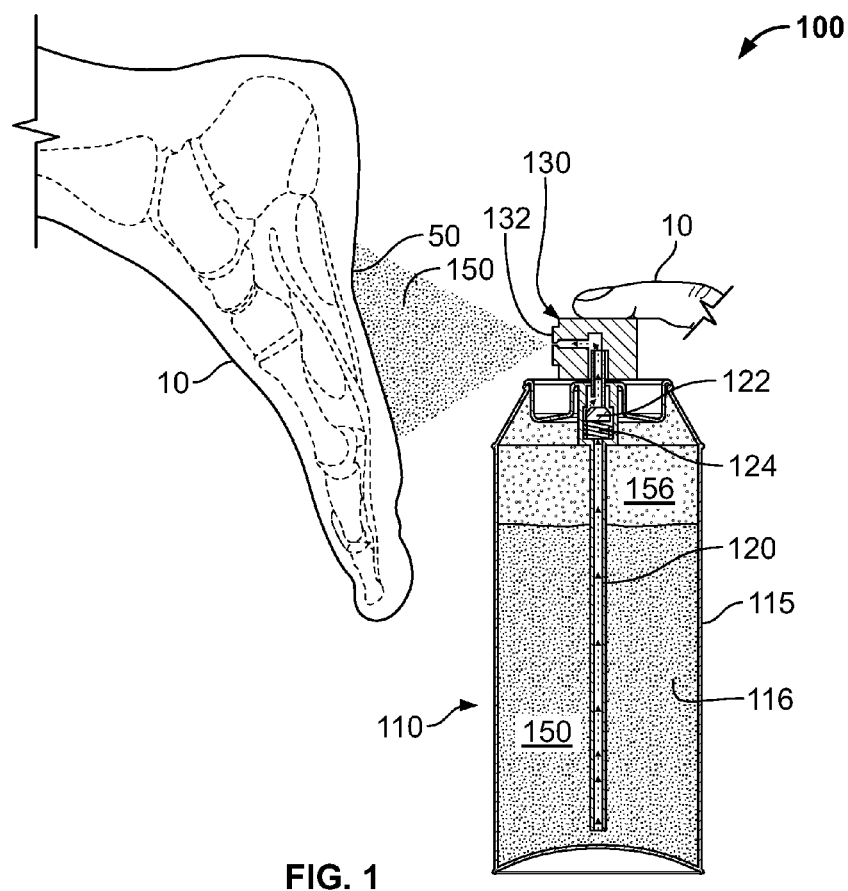
FIG. 1 is a cross-sectional view of a medical delivery device for applying a barrier composition to a targeted skin surface, in accordance with some embodiments.
Figures 2A, 2B:
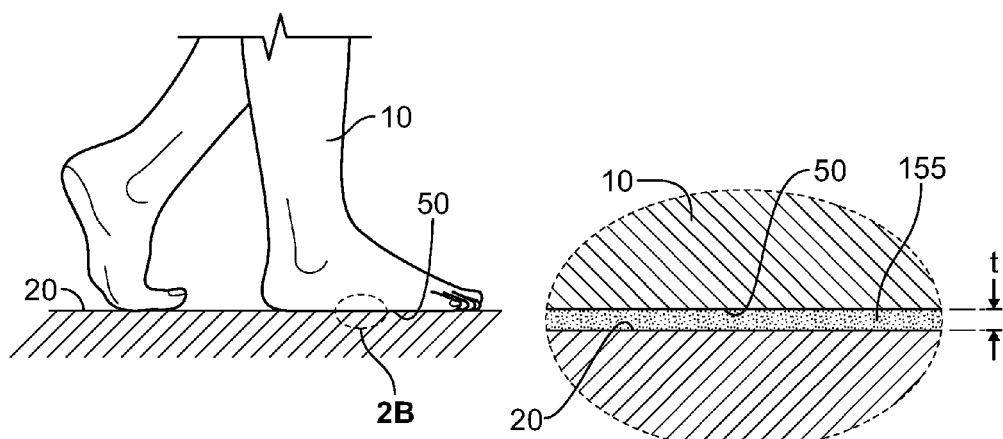
FIGS. 2A-B are sectional views of the barrier composition of FIG. 1 on the targeted skin surface.
Figure 6A:
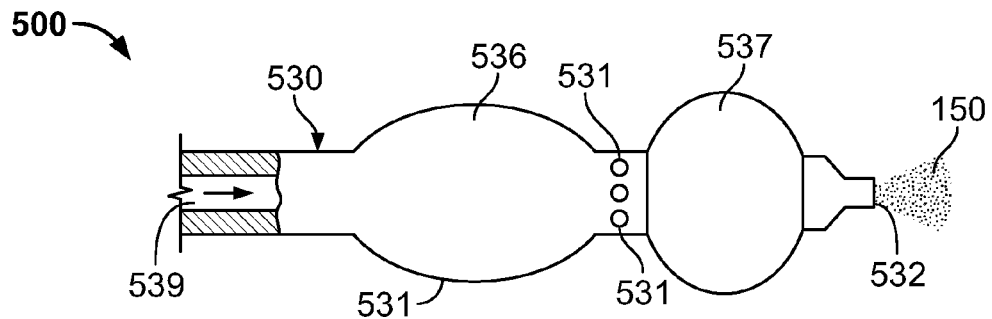
FIGS. 6A-C are partial cross-sectional views of another medical delivery device for applying a barrier composition to a targeted skin surface, in accordance with some embodiments.
Figure 6B:
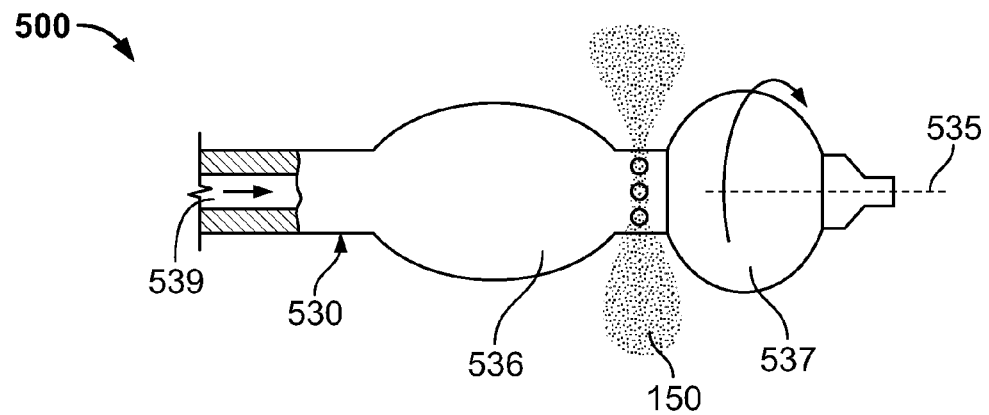
Figure 6C:
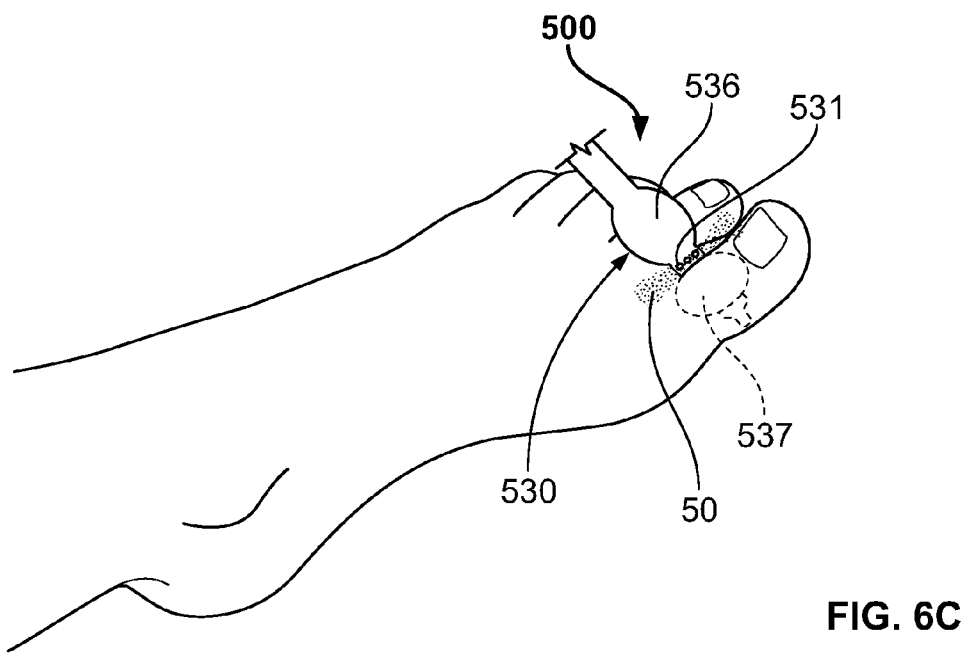

Referring to FIGS. 1 and 2A-B, a system 100 for applying a topical barrier layer to skin can include a medical delivery device 110 that can be carried and selectively activated by a user 10 to dispense a barrier composition 150 to a targeted skin surface 50. The medical delivery device 110 in this embodiment is configured to apply the barrier composition 150 to the targeted skin surface 50 so as to provide a protective layer 155 (FIG. 2B) affixed to an exterior of the skin surface 50 that reduces the likelihood of transmission of HPV or other microbial entities from a floor surface 20 or other external source to the user's skin surface 50. For example, the medical delivery device 110 in this embodiment is a topical spray applicator device having a reservoir 116 that contains the barrier composition 150 (e.g., a microbial-resistant barrier composition in this embodiment) so as to provide a substantially continuous barrier layer 155 (FIG. 2B) along targeted skin surface 50. As illustrated in the example of FIG. 1, the targeted skin surface 50 includes the bottom of the user's foot in this example, but it should be understood from the description herein that the medical delivery device 110 can be used to dispense the barrier composition to other targeted skin surfaces (e.g., elbows, hands, fingers, arms, legs, knees, or the like).

As described in more detail below, the barrier composition 150 can be formed as a liquid solution that can form a substantially uniform barrier layer 155 after topical application to the skin surface 50 and, optionally, contains one or more active agents to destroy or inhibit transmission of viruses (such as HPV) or other microbial entities. In such circumstances, the barrier layer formed on the skin surface 50 after dispensation from the medical delivery device 110 can provide both the barrier layer 155 of sufficient thickness to physically prevent penetration of HPV or other wart-causing microbial entities to the skin surface 50 (especially to any cut or otherwise compromised portions of the skin surface 50) and an anti-microbial effect that destroys or otherwise reduces the population of HPV or other microbial entities contacting or penetrating the barrier layer 155 or that otherwise inhibits infection from HPV or other microbial entities. As such, the barrier composition 150 serves to inhibit the attachment or adhesion of viruses (such as HPV) or other microbial entities to the skin surface 50, to inhibit the viruses (such as HPV) or other microbial entities from penetrating through the skin surface 50, and thus to inhibit possible infection from viruses (such as HPV) or other microbial entities.

The medical delivery device 110 can be configured to dispense the barrier composition 150 in a stream of particulate droplets, such as a fine mist spray in this example, so as to provide a substantially even coating of the barrier composition 150 along the targeted skin surface 150. In this example, during each application dispensed from the medical delivery device 110, the targeted skin surface 50 may include an area of greater than 12 square inches, and may essentially coat the entirety of the bottom the user's foot in the depicted example. In this embodiment, the barrier composition 150 sets into the layer 155 after application to the skin surface 50, and the barrier layer 155 optionally provides a non-tacky, generally transparent coating along the skin surface 50 that does not interfere with the user's normal actions (e.g., walking, swimming, etc.) when wearing the barrier layer 155. In some embodiments, the medical delivery device 110 is configured to dispense the barrier composition 150 at a volumetric application rate of about 1 $\mu L/cm^2$ to about 10 $\mu L/cm^2$, about 1 $\mu L/cm^2$ to about 5 $\mu L/cm^2$, about 2 $\mu L/cm^2$ to about 4 $\mu L/cm^2$, and preferably about 2 $\mu L/cm^2$ in this embodiment (depending upon the density of the formulation of the barrier composition 150). In such embodiments, the volumetric application rate from the medical delivery device can provide a layer thickness t (FIG. 2B) of about 5 microns to about 100 microns, about 5 microns to about 75 microns, about 10 microns to about 50 microns, and preferably about 20 microns to about 30 microns in this embodiment (depending upon the user's motion of the medical delivery device 110 during dispensation). In this embodiment, the layer thickness t (FIG. 2B) is a substantially uniform thickness over the targeted skin surface 50 and has a depth that is sufficient to provide a physical barrier between HPV and other microbial entities (passed from the floor surface 20) and the exterior of the skin surface 50. Moreover, as described in more detail below, some implementations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

As shown in FIG. 1, the medical delivery device 110 in this embodiment includes a container body 115 that defines a reservoir 116 for storing the barrier composition 150 therein. The reservoir 116 may also contain a propellant fluid 156, such as a hydrofluorocarbon (HFC) propellant. For example, the propellant fluid that is in a gaseous state at a compressed pressure inside the container 116, which thereby applies a pressure upon the liquid solution of the barrier composition 150 that urges the barrier composition 150 into the lumen of a flow tube 120. The flow tube 120 leads to a passage that is normally sealed by a plunger 122, which in this embodiment is biased to the sealed position by a spring member 124. As shown in FIG. 1, when the user 10 actuates the head of a nozzle 130, the plunger 122 is moved away from the sealed position and the fluid path from the flow tube 120 to the exit port 132 of the nozzle 130 is opened. The exit port 132 of the nozzle 130 can be configured to dispense the barrier composition 150 in a stream of particulate droplets, such as a fine mist spray, so as to provide a substantially even coating of the barrier composition 150 along the targeted skin surface 150. When the user releases the head of the nozzle 130, the spring member 124 urges the plunger 122 to return to the sealed position that closed the flow path, and the remainder of the barrier composition in the reservoir 116 is sealed from the ambient surroundings and stored for a subsequent use.

Referring now to FIG. 3, some embodiments of a system 200 for applying a topical barrier layer to skin can include a medical delivery device 210 that stores the barrier composition 150 in isolation from the propellant fluid 156. Similar to the previously described embodiment depicted in FIG. 1, the medical delivery device 210 in this embodiment is a topical spray applicator that operates to dispense the barrier composition 150 to the targeted skin surface 50 so as to provide a protective layer 155 (FIG. 2B) affixed to an exterior of the skin surface 50 that reduces the likelihood of transmission of HPV or other microbial entities from a floor surface 20 or other external source to the user's skin surface 50.

As shown in FIG. 3, the medical delivery device 210 in this embodiment includes a container body 215 that defines a reservoir 217 for storing the barrier composition 150 therein. The container body 215 may also provide an isolated reservoir 216 for a propellant fluid 256, such as a propellant gas. As such, the barrier composition 150 can be maintained under pressure in the first reservoir 217 without necessarily interacting with (or reacting with) the propellant fluid 156. For example, the reservoir 217 containing the barrier composition 150 is separated from the second reservoir 216 by a slidable seal disc 220 that is biased toward the barrier composition 150 due to the elevated fluid pressure of the propellant fluid 156 in the second reservoir 216. Accordingly, the disc 220 applies a pressure upon the liquid solution of the barrier composition 150 that urges the barrier composition 150 toward the flow path through the nozzle 230 when the plunger 222 is actuated by a user depressing the actuator head 231 of the nozzle 230. In this embodiment, the container body 215 can define a first fill port 228 in communication with the first reservoir 217, and a second fill portion 218 in communication with the second reservoir 216. The first fill port 228 is separated from the second fill port 218 by the disc 220, and each of the fill ports 218 and 228 are equipped with a ball valve that is biased to a sealed position. Thus, during manufacture of the device 210, a first connector can join with the first fill port 228 to dispense the barrier composition 150 into the first reservoir 217 (in which case the ball valve is temporarily opened). Similarly, a second connector can join with the second fill port 218 to dispense the propellant fluid 156 into the second reservoir (in which case the ball valve is temporarily opened) in isolation from the barrier composition 150.

As shown in FIG. 3, when the user actuates the head 231 of a nozzle 230, the plunger 222 is moved away from the sealed position and the fluid path from the reservoir 217 to the exit port 232 of the nozzle 230 is opened. The exit port 232 of the nozzle 230 can be configured to dispense the barrier composition 150 in a stream of particulate droplets, such as a fine mist spray, so as to provide a substantially even coating of the barrier composition 150 along the targeted skin surface 150 (FIGS. 2A-B). When the user releases the head of the nozzle 230, a spring diaphragm portion 223 of the plunger biases the plunger 222 to return to the sealed position that closed the flow path, and the remainder of the barrier composition 150 in the reservoir 217 is sealed from the ambient surroundings and stored for a subsequent use.

Similar to the previously described embodiment in FIG. 1, the medical delivery device 210 can be configured to dispense the barrier composition 150 to provide a substantially even coating of the barrier composition 150 along the targeted skin surface 150. The medical delivery device 210 may optionally be configured to dispense the barrier composition 150 at a volumetric application rate of about 1 $\mu L/cm^2$ to about 10 $\mu L/cm^2$, about 1 $\mu L/cm^2$ to about 5 $\mu L/cm^2$, about 2 $\mu L/cm^2$ to about 4 $\mu L/cm^2$, and preferably about 2 $\mu L/cm^2$ in this embodiment (depending upon the density of the formulation of the barrier composition 150). In such embodiments, the volumetric application rate from the medical delivery device 210 can provide a layer thickness t (FIG. 2B) of about 5 microns to about 100 microns, about 5 microns to about 75 microns, about 10 microns to about 50 microns, and preferably about 20 microns to about 30 microns in this embodiment (depending upon the user's motion of the medical delivery device 210 during dispensation). In this embodiment, the layer thickness t (FIG. 2B) is a substantially uniform thickness over the targeted skin surface 50 and has a depth that is sufficient to provide a physical barrier between HPV and other microbial entities (passed from the floor surface 20) and the exterior of the skin surface 50. Moreover, as described in more detail below, some implementations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

Referring now to FIG. 4, some embodiments of a system 300 for applying a topical barrier layer to skin can include a medical delivery device 310 that stores the barrier composition 150 under pressure without the use of a propellant fluid. Similar to the previously described embodiment depicted in FIG. 3, the medical delivery device 310 in this embodiment is a topical spray applicator that operates to dispense the barrier composition 150 to the targeted skin surface 50 so as to provide a protective layer 155 (FIG. 2B) affixed to an exterior of the skin surface 50 that reduces the likelihood of transmission of HPV or other microbial entities from a floor surface 20 or other external source to the user's skin surface 50. The medical delivery device 310 in this embodiment includes a container body 315 that defines a reservoir 317 for storing the barrier composition 150 therein. In this embodiment, the container body 315 can define a first fill port 328 in communication with the reservoir 317, and the fill port 328 is equipped with a ball valve that is biased to a sealed position. Thus, during manufacture of the device 210, a first connector can join with the first fill port 328 to dispense the barrier composition 150 into the reservoir 317 (in which case the ball valve is temporarily opened). The container body 315 may also provide a space that houses at least one spring member 356, such as a coil spring, that applies a pressure to the barrier composition 150 in the reservoir 317. As such, the barrier composition 150 can be maintained under pressure in the reservoir 317 without necessarily using any propellant fluid. In this embodiment, the reservoir 317 containing the barrier composition 150 is separated from the spring member 356 by a slidable seal disc 320 that is biased toward the barrier composition 150 due to the force from the compressed spring member 356. Accordingly, the disc 320 applies a pressure upon the liquid solution of the barrier composition 150 that urges the barrier composition 150 toward the flow path through the nozzle 330 when the plunger 322 is actuated by a user depressing the actuator head 331 of the nozzle 330.

As shown in FIG. 4, when the user actuates the head 331 of a nozzle 330, the plunger 322 is moved away from the sealed position and the fluid path from the reservoir 317 to the exit port 332 of the nozzle 330 is opened. The exit port 332 of the nozzle 330 can be configured to dispense the barrier composition 150 in a stream of particulate droplets, such as a fine mist spray, so as to provide a substantially even coating of the barrier composition 150 along the targeted skin surface 150 (FIGS. 2A-B). When the user releases the head of the nozzle 330, a spring diaphragm portion 323 of the plunger biases the plunger 322 to return to the sealed position that closed the flow path, and the remainder of the barrier composition 150 in the reservoir 317 is sealed from the ambient surroundings and stored for a subsequent use.

Similar to the previously described embodiments in FIGS. 1 and 3, the medical delivery device 310 can be configured to dispense the barrier composition 150 to provide a substantially even coating of the barrier composition 150 along the targeted skin surface 150. The medical delivery device 310 can be configured to dispense the barrier composition 150 at a volumetric application rate of about 1 $\mu L/cm^2$ to about 10 $\mu L/cm^2$, about 1 $\mu L/cm^2$ to about 5 $\mu L/cm^2$, about 2 $\mu L/cm^2$ to about 4 $\mu L/cm^2$, and preferably about 2 $\mu L/cm^2$ in this embodiment (depending upon the density of the formulation of the barrier composition 150). In such embodiments, the volumetric application rate from the medical delivery device 310 can provide a layer thickness t (FIG. 2B) of about 5 microns to about 100 microns, about 5 microns to about 75 microns, about 10 microns to about 50 microns, and preferably about 20 microns to about 30 microns in this embodiment (depending upon the user's motion of the medical delivery device 310 during dispensation). In this embodiment, the layer thickness t (FIG. 2B) is a substantially uniform thickness over the targeted skin surface 50 and has a depth that is sufficient to provide a physical barrier between HPV and other microbial entities (passed from the floor surface 20) and the exterior of the skin surface 50. Moreover, as described in more detail below, some implementations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

Referring now to FIGS. 5A-B, some embodiments of a system 400 for applying a topical barrier layer to skin can include a medical delivery device 410 that provides an applicator instrument 430 separable from a reservoir 416 containing the barrier composition 150. In the depicted embodiment, the medical delivery device 410 includes a roller sponge applicator 430 configured to absorb a portion of the barrier composition from the reservoir 416 in the container body 415 (FIG. 5A) and then to directly contact the targeted skin surface 50 to dispense a substantially even coating of the barrier composition thereto (FIG. 5B). As such, the medical delivery device 410 operates to dispense the barrier composition 150 to the targeted skin surface 50 so as to provide a protective layer 155 (FIG. 2B) affixed to an exterior of the skin surface 50 that reduces the likelihood of transmission of HPV or other microbial entities from a floor surface 20 or other external source to the user's skin surface 50.

As shown in FIG. 5A, the medical delivery device 410 in this embodiment includes the container body 415 that defines the reservoir 416 containing the barrier composition 150. The container body 415 can include a threaded neck region 420 that mates with a corresponding thread pattern of a handle 431 of the applicator instrument 430. When the actuator instrument 430 is mated with the container body 415, the reservoir 416 is sealed and the barrier composition 150 can be stored without being under pressure (e.g., under pressure from a propellant fluid or a spring-bias device). Also, when the actuator instrument 430 is mated with the container body 415, a sponge applicator member 432 of the applicator instrument 430 is submerged into the liquid solution of the barrier composition 150 so that a portion of the barrier composition 150 is absorbed by porous regions of sponge applicator member 432.

As shown in FIG. 5B, the applicator 430 can be disengaged from the container body 415 so that the sponge applicator member 432 is exposed. In this embodiment, the sponge applicator member 432 is movable relative to the handle 431 of the application instrument 430. For example, the sponge applicator member 432 can be rotatable relative to the handle 431 about a longitudinal axis 435 of the applicator instrument 430 while the user grasps the handle 431. As such, the applicator instrument 430 can be moved over the targeted skin surface 50 so that the applicator member 432 directly contacts the targeted skin surface 50 (e.g., and optionally rolls along the skin surface 50) to dispense a substantially even coating of the barrier composition 150 thereto (FIG. 5B). After the barrier composition 150 is applied to the skin surface and allowed to set into a fully form barrier layer 155 (refer to the example in FIG. 2B), the layer thickness t (FIG. 2B) can be a substantially uniform thickness over the targeted skin surface 50 and preferably has a depth that is sufficient to provide a physical barrier between HPV and other microbial entities (passed from the floor surface 20) and the exterior of the skin surface 50. Moreover, as described in more detail below, some implementations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

Referring now to FIGS. 6A-B, some embodiments of a system 500 for applying a topical barrier layer to skin can include a nozzle device 530 configured to attach with a spray applicator device so as to dispense the barrier composition 150 from user-selectable ports 531 or 532. For example, the nozzle device 530 can be assembled as part of (or releasably attached to) the spray applicators described above in connection with any of FIGS. 1, 3, and 4. In such embodiments, the user can selected the different dispensation ports 531 or 532 so as to more conveniently dispense the barrier composition 150 to different portions of the targeted skin surface (e.g., the relatively flat portions of the bottom of the foot versus areas between the toes that might be more susceptible to penetration of HPV and subsequent wart growth). Similar to the nozzle devices 130, 230, and 330 the previously described embodiments depicted in FIGS. 1, 3, and 4 (respectively), the nozzle device 530 is configured to dispense the barrier composition 150 to the targeted skin surface 50 so as to provide a protective layer 155 (FIG. 2B) affixed to an exterior of the skin surface 50 that reduces the likelihood of transmission of HPV or other microbial entities from a floor surface 20 or other external source to the user's skin surface 50. The topical spray applicator used in conjunction with the nozzle device 530 in this embodiment includes a container body that defines a reservoir for storing the barrier composition 150 therein. Accordingly, the fluid path from the reservoir to the nozzle device 530 is opened (via actuation from the user as described above), the barrier composition 150 is dispensed from either the intermediate exit ports 531 (FIG. 6B) or the distal exit port 532 (FIG. 6A). The distal exit port 532 of the nozzle 530 is configured to dispense the barrier composition 150 in a generally distal direction as a stream of particulate droplets, such as a fine mist spray. The intermediate exit ports 531 in this embodiment are positioned between two bulbous portions 536 and 537, and the intermediate exit ports 531 of the nozzle 330 are configured to dispense the barrier composition 150 in a generally radial direction. The different spray patterns and directions provided by either the intermediate ports 531 or the distal port 532 provide advantageous options for the user when dispensing the barrier composition to different regions of the targeted skin surface 50.

In this embodiment, the user can select whether the barrier composition 150 should exit from the intermediate ports 531 or the distal port 532 by rotatably adjusting the second bulbous portion 537 about a longitudinal axis 535 of the nozzle device 530. For example, when the second bulbous portion 537 is arranged in a first position (FIG. 6A), the distal exit port 532 is open to the fluid lumen 539 while the intermediate ports 531 are closed to the fluid lumen 539. Also, when the second bulbous portion 537 is rotated to a second position (FIG. 6B), the intermediate ports 531 are open to the fluid lumen 539 while the distal exit port 532 is closed to the fluid lumen 539. The distal exit port 532 can be configured to dispense the barrier composition 150 to the targeted skin surface in manner similar to that depicted in FIG. 1. The user can then adjust the nozzle device 530 so that the barrier composition 150 dispenses from the intermediate ports 531. In one example depicted in FIG. 6C, the first and second bulbous portions 536 and 537 can be engaged with two adjacent toes (or other body parts in need of being spread apart during dispensation of the barrier composition) so that one of the bulbous portions 536 or 537 is positioned dorsal of an inter-digital web surface between the toes and the other of the bulbous portions 536 or 537 is positioned ventral of the inter-digital web surface between the toes. In doing so, the bulbous portions 536 and 537 may partially spread apart the adjacent toes, thereby more fully exposing the skin surface between the toes to the barrier composition 150 as it is sprayed from the intermediate ports 531. In this example, the intermediate ports 531 can be generally aligned with the skin surface between the toes due to the position relative to the two bulbous portions 536 and 537. (Note that, in the depiction in FIG. 6C, the ports 531 are shown at a particular location relative to the inter-digital web surface between the toes for purposes of illustration, and that the ports 531 can be located more toward an underside of the inter-digital web surface between the toes during use of the nozzle device 530.)

Similar to the previously described embodiments in FIGS. 1, 3, and 4, the nozzle device 530 can be configured to dispense the barrier composition 150 to provide a substantially even coating of the barrier composition 150 along the targeted skin surface 150. The topical spray applicator used in conjunction with the nozzle device 530 can be configured to dispense the barrier composition 150 at a volumetric application rate of about 1 µL/cm$^2$ to about 10 µL/cm$^2$, about 1 µL/cm$^2$ to about 5 µL/cm$^2$, about 2 µL/cm$^2$ to about 4 µL/cm$^2$, and preferably about 2 µL/cm$^2$ in this embodiment (depending upon the density of the formulation of the barrier composition 150). In such embodiments, the volumetric application rate from the nozzle device 530 can provide a layer thickness t (FIG. 2B) of about 5 microns to about 100 microns, about 5 microns to about 75 microns, about 10 microns to about 50 microns, and preferably about 20 microns to about 30 microns in this embodiment (depending upon the user's motion of the nozzle device 530 during dispensation). In this embodiment, the layer thickness t (FIG. 2B) is a substantially uniform thickness over the targeted skin surface 50 and has a depth that is sufficient to provide a physical barrier between HPV and other microbial entities (passed from the floor surface 20) and the exterior of the skin surface 50. Moreover, as described in more detail below, some implementations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

Figure 7A:
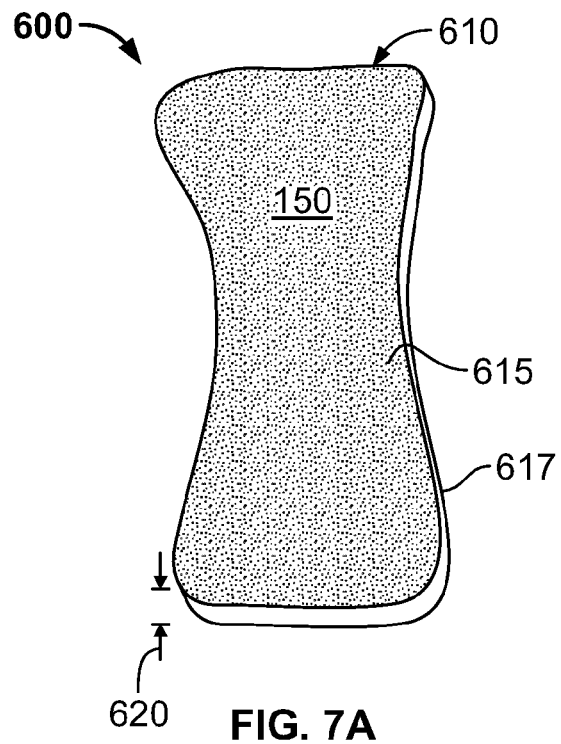
FIGS. 7A-B are perspective and top views, respectively, of another medical delivery device for applying a barrier composition to a targeted skin surface, in accordance with some embodiments.
Figure 7B:
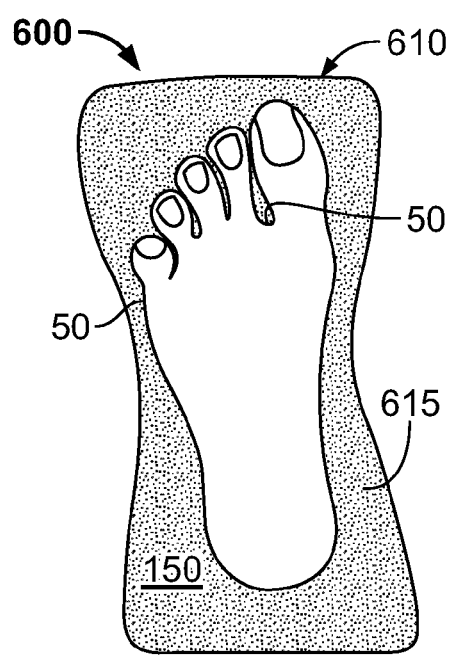

Referring now to FIGS. 7A-B, some embodiments of a system 600 for applying a topical barrier layer to skin can include a medical delivery device 610 that provides a disposable applicator pad (e.g., an absorbent sponge material, an absorbent gauze pad, a thick fibrous web, or the like) impregnated with the barrier composition 150. In the depicted embodiment, the medical delivery device 610 is configured to be removed from a sealed package and then directly contacted to the targeted skin surface 50 to dispense a substantially even coating of the barrier composition thereto (FIG. 7B). As such, the medical delivery device 610 operates to dispense the barrier composition 150 to the targeted skin surface 50 so as to provide a protective layer 155 (FIG. 2B) affixed to an exterior of the skin surface 50 that reduces the likelihood of transmission of HPV or other microbial entities from a floor surface 20 or other external source to the user's skin surface 50.

The medical delivery device 610 in this embodiment includes a container body in the form of a disposable applicator pad impregnated with the barrier composition 150 and having a peripheral shape that is contoured to match particular body parts. In this example, the disposable applicator pad 610 has a contoured periphery and a surface area that corresponds to the bottom of a user's foot. As such, the user can remove the disposable applicator pad 610 from a sealed packaging, rest the disposable applicator pad 610 on the floor in a generally flat condition (FIG. 7A), and then step onto a major upper surface 615 of the disposable applicator pad 610 so that at least a portion of the barrier composition 150 transfers to the targeted skin surface 50 on the bottom of the user's foot. In these circumstances, the regions along the bottom of the user's foot are substantially similar to the regions of the foot that would normally contact the floor 20 (FIGS. 2A-B) during the user's normal activities, so the disposable applicator pad 610 is configured to apply the barrier composition 150 directly to those specific portion of the user's foot that would normally be more susceptible to exposure to HPV and other microbial entities. In this embodiment, the disposable applicator pad 610 has a thickness 620 and porosity along the upper major surface 615 so that the disposable applicator pad 610 is configured to absorb and retain a dosage of the barrier composition 150 until it is compressed against the targeted skin surface 50. As such, the porous regions of the disposable applicator pad 610 proximate to the upper major surface 615 can operate as the reservoir for retaining the barrier composition 150 prior to dispensation to the targeted skin surface 50. For example, the disposable applicator pad 610 may have a thickness 620 of about 0.5 mm to about 10 mm, about 1 m to about 5 mm, and preferably about 1 mm to about 3 mm in this embodiment. A lower major surface 617 of the disposable applicator pad 610 can include an impermeable material so that the liquid solution of the barrier composition 150 does not escape through the lower major surface 617 during the dispensation of the barrier composition from the upper major surface 615. As illustrated in the example of FIG. 7B, the targeted skin surface 50 includes the bottom of the user's foot in this example, but it should be understood from the description herein that the disposable applicator pad 610 can be engaged with other targeted skin surfaces (e.g., elbows, hands, fingers, arms, legs, knees, or the like) so as to dispense the barrier composition 150.

After the barrier composition 150 is applied to the skin surface 50 from the disposable applicator pad 610 and allowed to set into a fully form barrier layer 155 (refer to the example in FIG. 2B), the barrier layer thickness t (FIG. 2B) can be a substantially uniform thickness over the targeted skin surface 50 and preferably has a depth that is sufficient to provide a physical barrier between HPV and other microbial entities (passed from the floor surface 20) and the exterior of the skin surface 50. Moreover, as described in more detail below, some implementations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

Figure 8:
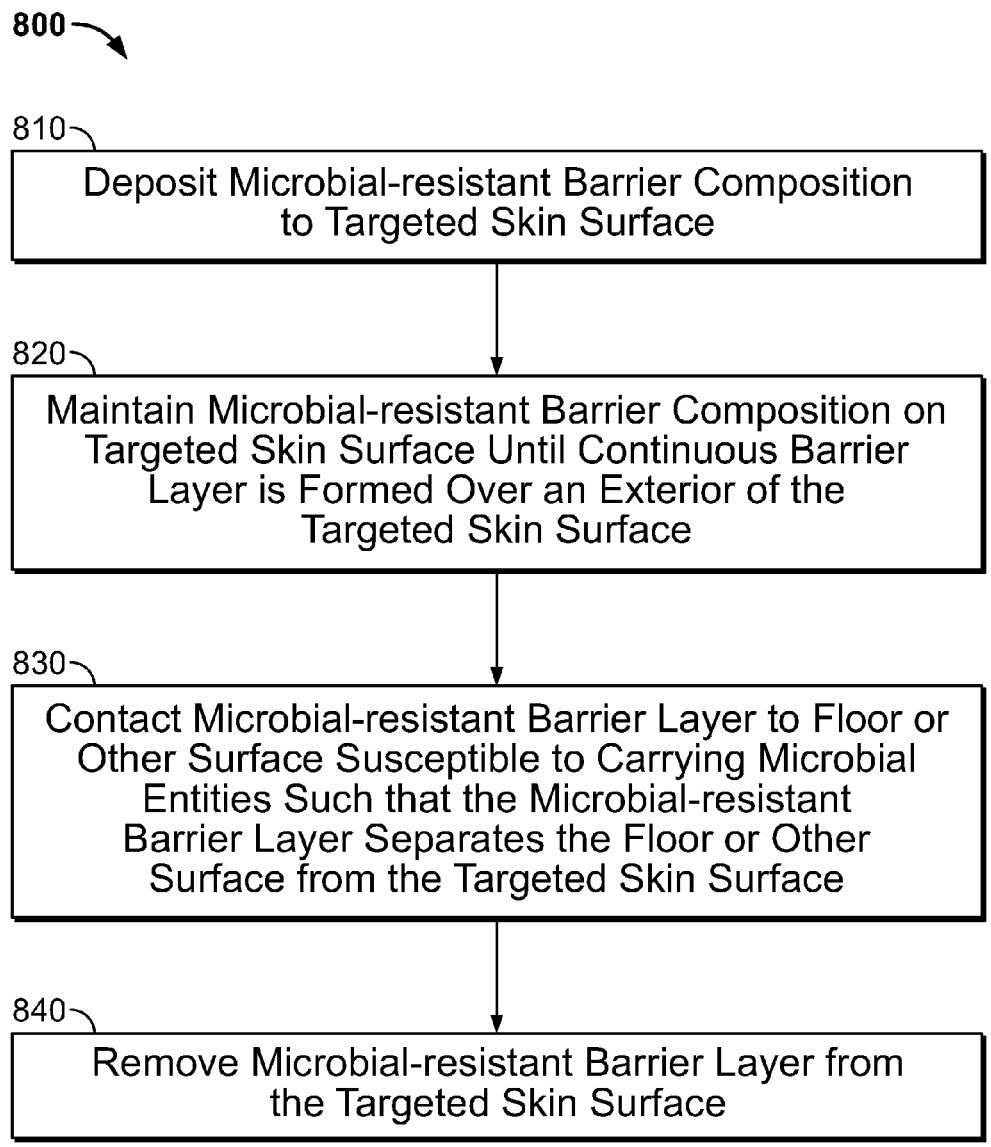
FIG. 8 is a chart of a method for applying a barrier composition to a targeted skin surface, in accordance with some embodiments.

Referring now to FIG. 8, some embodiments of a method 800 of using a barrier composition on a targeted skin surface can include a step 810 of depositing a barrier composition (e.g., a microbial-resistant barrier composition in this embodiment) to a targeted skin surface. For example, as described in connection with FIGS. 2A-B, a medical delivery device (examples described above, for example, in FIGS. 1 and 3-7B) can be configured to deposit the barrier composition 150 to provide a coating of the barrier composition 150 along the targeted skin surface 150. Depending upon the medical delivery device used in the method 800, the barrier composition 150 may optionally be dispensed at a volumetric application rate of about 1 µL/cm$^2$ to about 10 µL/cm$^2$, about 1 µL/cm$^2$ to about 5 µL/cm$^2$, about 2 µL/cm$^2$ to about 4 µL/cm$^2$, and preferably about 2 µL/cm$^2$.

The method 800 may also include the step 820 of maintaining the microbial-resistant barrier composition on the targeted skin surface until a barrier layer is formed over an exterior of the targeted skin surface. In this embodiment, the barrier layer 155 (refer, for example, to FIG. 2B) is preferably a continuous barrier layer. For example, depending upon the medical delivery device used in the method 800 and the user's motion of the medical delivery device during dispensation, the barrier composition 150 may optionally deposited onto the targeted skin surface 50 to provide durable barrier layer having thickness t (FIG. 2B) of about 5 microns to about 100 microns, about 5 microns to about 75 microns, about 10 microns to about 50 microns, and preferably about 20 microns to about 30 microns in this embodiment. Preferably, the layer thickness t has a depth that is sufficient to provide a physical barrier between HPV and other microbial entities (passed from the floor surface 20) and the exterior of the skin surface 50.

Still referring to FIG. 8, the method 800 may further include the step 830 of contacting the barrier layer to a floor or other surface susceptible to carrying HPV or other microbial entities. The barrier layer in this step may act as a microbial-resistant barrier layer. For example, the microbial-resistant barrier layer 155 (refer to FIG. 2b) can separate the floor 20 or other surface from the targeted skin surface 50, thereby hindering HPV or other microbial entities from reaching the targeted skin surface 50 or penetrating any compromised portions of the targeted skin surface 50. Also, as described in more detail below, some implementations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

The method 800 may also include the step 840 of removing the barrier layer from the targeted skin surface. For example, the barrier layer 155 (FIG. 2) may be formed as a durable coating over the skin surface 50 that maintains its barrier effects even when the user walks barefoot on the floor 20 for an extended period of time (e.g., more than 30 minutes, more than 45 minutes, more than 60 minutes, and preferably about 30 minutes to about 240 minutes in this embodiment). Such a coating of the barrier layer 155 may be durable and resistant to wear when the user is barefoot or wearing shoes or socks during the aforementioned time period, and furthermore such a coating of the barrier layer 155 can be resistant to perspiration and prolonged exposure to water during the aforementioned time period. In such circumstances, the barrier layer 155 can be removed by washing the targeted skin surface with soap and water so as to breakdown the barrier layer. In other implementations, the barrier layer 155 can be removed by soaking the targeted skin surface is a barrier removal solution, by exposing the barrier layer to scrubbing friction (e.g., using a pumice stone, a cloth, or the like), by exposing the barrier layer to a body lotion or body oil, or the like.

As described in the aforementioned embodiments, the barrier composition 150 can be dispensed to the targeted skin surface using a number of different medical delivery devices, depending upon the properties of the barrier composition 150, its preferred storage conditions, and a number of other factors that should be understood from the description herein. In some embodiments, the barrier composition 150 is formulated to set into a durable protective layer 155 (FIG. 2b) after application to the skin surface 50, and the barrier layer 155 may optionally a non-tacky, generally transparent coating along the skin surface 50 that does not interfere with the user's normal actions (e.g., walking, swimming, etc.) when wearing the barrier layer 155. Also, the barrier layer 155 is preferably formed with a thickness that is sufficient to provide a physical barrier between HPV and other microbial entities (passed from the floor surface 20) and the exterior of the skin surface 50. Moreover, as described in more detail below, some formulations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities.

In some implementations, the barrier composition 150 can include a vehicle, a preservative, and an active agent. In some cases, the barrier composition 150 includes a vehicle, an emulsifier, a preservative, and an active agent. For example, the barrier composition 150 can include a hydrophobic carrier, water, an emulsifier, a preservative, and an active agent.

A vehicle, as provided herein, refers to pharmaceutically acceptable carrier materials suitable for topical administration. Vehicles useful herein include materials that are non-toxic and that do not interact with other components of the composition in a deleterious manner.

The barrier composition 150 can include from about 30% to about 90% by weight of a vehicle. For example, the vehicle can be present in an amount ranging from about 40% to about 80% by weight of the barrier composition (e.g., from about 40% to about 75%, from about 40% to about 65%, from about 40% to about 60%, from about 40% to about 55%, from about 45% to about 80%, from about 50% to about 80%, from about 55% to about 80%, from about 60% to about 80%, from about 45% to about 75%, from about 50% to about 70%, from about 55% to about 65% by weight of the carrier composition). In some embodiments, the vehicle is present in an amount sufficient to bring the total amount of components in the composition up to 100% by weight of the barrier composition 150.

In some embodiments, a vehicle includes one or more hydrophobic carriers and one or more aqueous carriers. For example, the vehicle can include one or more hydrophobic carriers and water.

Non-limiting examples of hydrophobic carriers of the barrier composition 150 include: mineral oil, petrolatum, vegetable oils, natural waxes (e.g., vegetable waxes), triglycerides, and esters. For example, the hydrophobic carrier can be a vegetable oil such as almond oil, apricot oil, avocado oil, black cumin oil (e.g., virgin black cumin oil), black currant oil, castor oil, cherry kernel oil, emu oil, grape seed oil, grapefruit seed oil, hazelnut oil, jojoba oil, kukui nut oil, macadamia nut oil, meadowfoam seed oil, peach kernel oil, pecan oil, perilla seed oil, pistachio oil, pomegranate seed oil, pumpkin seed oil, raspberry oil, red palm olein, rice bran oil, rosehip oil, seabuckthorn fruit oil (e.g., virgin seabuckthorn fruit oil), shea olein, sunflower oil, or walnut oil. Examples of natural waxes include beeswax, candelilla wax, carnauba wax, castor wax flakes, emulsifying wax, soy wax, and lanolin. In some embodiments, the hydrophobic carrier is selected from the group consisting of: castor oil, sunflower oil, olive oil, corn oil, soybean oil, canola oil, cottonseed oil, coconut oil, babassu oil, palm kernel oil, sesame oil, borage seed oil, syzigium aromaticum oil, hempseed oil, flaxseed oil, wheat germ oil, evening primrose oil glycerin, silicone oils, beeswax, triglycerides (e.g., caprylic capric triglycerides), and mixtures of two or more thereof. In some embodiments, a vehicle is selected from mineral oil, vegetable oil, castor oil, sunflower oil, caprylic capric triglycerides, and mixtures of two or more thereof.

A hydrophobic carrier can be present in the barrier composition 150 in an amount ranging from about 5% to about 80% by weight of the barrier composition. For example, the amount of the hydrophobic carrier can range from about 10% to about 50% by weight of the barrier composition (e.g., from about 5% to about 45%, from about 5% to about 40%, from about 5% to about 35%, from about 5% to about 30%, from about 5% to about 27%, from about 5% to about 25%, from about 5% to about 22%, from about 5% to about 20%, from about 10% to about 50%, from about 15% to about 50%, from about 18% to about 50%, from about 20% to about 50%, from about 25% to about 50%, from about 30% to about 50%, from about 35% to about 50%, from about 40% to about 50%, from about 10% to about 35%, from about 15% to about 30%, from about 17% to about 27%, and from about 20% to about 30% by weight of the barrier composition). In some embodiments, the vehicle ranges from about 10% to about 30% by weight of the barrier composition 150.

An aqueous carrier can include water, glycerin, propylene glycol, butylene glycol, caprylyl glycol, decylene glycol, pentylene glycol, benzyl alcohol, methanol, ethanol, isopropanol, denatured alcohol, and mixtures thereof. In some embodiments, the aqueous carrier is water.

The amount of an aqueous carrier (e.g., water) used in the barrier composition 150 as provided herein can be an amount sufficient (q.s.) to bring the composition to 100% by weight. For example, the amount of an aqueous carrier can range from about 35% to about 80% by weight of the barrier composition. For example, the aqueous carrier can range from about 40% to about 75% by weight (e.g., from about 40% to about 70%, from about 40% to about 65%, from about 40% to about 60%, from about 40% to about 55%, from about 45% to about 75%, from about 50% to about 75%, from about 55% to about 75%, from about 45% to about 65%, from about 50% to about 70%, and from about 50% to about 60% by weight of the barrier composition). In some embodiments, the amount of aqueous carrier ranges from about 45% to about 60% by weight of the barrier composition 150.

In some embodiments, the aqueous carrier of the barrier composition 150 is water. The amount of water used in the barrier composition 150 as provided herein can be an amount sufficient (q.s.) to bring the composition to 100% by weight. For example, the amount of water can range from about 35% to about 80% by weight of the barrier composition 150. For example, the aqueous carrier can range from about 40% to about 75% by weight (e.g., from about 40% to about 70%, from about 40% to about 65%, from about 40% to about 60%, from about 40% to about 55%, from about 45% to about 75%, from about 50% to about 75%, from about 55% to about 75%, from about 45% to about 65%, from about 50% to about 70%, and from about 50% to about 60% by weight of the barrier composition). In some embodiments, the amount of water ranges from about 45% to about 60% by weight of the barrier composition 150.

Some embodiments of the barrier composition 150 as provided herein can further include a preservative. The preservative may be a compound that can prevent or inhibit the barrier composition or one or more components included in the barrier composition from decomposing due to microbial growth or undesirable chemical change. Non-limiting examples of preservatives include: butylated hydroxytoluene (BHT), benzalkonium chloride (BAC), a paraben (e.g., one or more of methylparaben, ethylparaben, isopropylparaben, isobutylparaben, heptylparaben, benzylparaben, butylparaben, and pharmaceutically acceptable salts thereof), and isothiazolinones (e.g., chloromethylisothiazolinone (CMIT) and methylisothiazolinone (MIT)).

The preservative can be present in an amount sufficient to prevent decomposition as described herein. For example, the amount of preservative can range from about 0.5% to about 5% by weight of the barrier composition (e.g., from about 0.5% to about 3%, from about 0.5% to about 2.5%, from about 0.5% to about 2%, from about 0.5% to about 1.5%, from about 0.5% to about 1%, from about 0.75% to about 5%, from about 1% to about 5%, from about 1.5% to about 5%, from about 2% to about 5%, from about 0.75% to about 1.5%, from about 1% to about 3%, and from about 2% to about 4% by weight of the barrier composition). In some embodiments, the amount of preservative can range from about 0.75% to about 1.5% by weight of the barrier composition 150. For example, the preservative can be present in an amount of about 1% by weight of the barrier composition 150.

Some embodiments of the barrier composition 150 as provided herein may further include an active agent. The active agent can include one or more pharmaceutically acceptable compounds or compositions that are capable of preventing the transmission of, or capable of destroying, microbial entities that might otherwise penetrate through a skin surface and cause skin warts. In particular embodiments, one or active agents of the barrier composition 150 can be a virucidal or virostatic agent that can inhibit infection from viruses (such as HPV) or other microbial entities. For example, active agents include compounds or compositions capable of reducing the likelihood of transmission of viruses (such as HPV) or other microbial entities. Non-limiting examples of active agents include: dextran (e.g., dextran hydrogel), butylated hydroxytoluene (BHT), benzalkonium chloride (BAC), monolaurin, vitamin A and other retinoids (e.g., retinoic acid, isoretinoic acid, and retinol), vitamin B12, garlic, Echinacea (e.g. an Echinacea extract), cimetidine, cidofovir, chlorphenesin, bisabolol, lysine, resveratrol, carrageenans, linear sulphated polysaccharides, fluorouracil, linear sulphated polysaccharides, tea tree oil, vitamin E, lemon oil, hydrogel, aloe vera, apple cider vinegar, *podophyllum, thuja oil, silicone,* 3-(trihydroxysilyl) propyldimethyloctadecyl ammonium chloride, sodium benzoate, sorbic acid, imidurea, potassium sorbate, phenoxyethanol, benzyl alcohol, bronopol, dehydroacetic acid, DMDM hydantoin, iodopropynyl butylcarbamate, polyaminopropyl biguanide, methylisothiazolinone, benzisothiazolinone, and mixtures of two or more thereof. In some embodiments, an active agent is selected from the group consisting of: monolaurin, Echinacea (e.g., Echinacea extract), cimetidine, dextran (e.g., dextran hydrogel), resveratrol, benzalkonium chloride (BAC), *podophyllum, tea tree oil, thuja oil, and mixtures of two or more thereof.*

An active agent may be present in the barrier composition 150 in an amount effective to prevent warts and/or reduce the transmission of HPV and other microorganisms. In some embodiments, an active agent can be present in an amount ranging from about 0.1% to about 10% by weight of the barrier composition 150. For example, an active agent can be present in an amount ranging from about 0.5% to about 5% by weight of the barrier composition (e.g., from about 0.5% to about 4%, from about 0.5% to about 3%, from about 0.5% to about 2%, from about 0.5% to about 1.5%, from about 0.5% to about 1%, from about 0.75% to about 5%, from about 1% to about 5%, from about 1.5% to about 5%, from about 2% to about 5%, from about 3% to about 5%, from about 0.75% to about 2.5%, from about 1% to about 4%, from about 1.5% to about 3.5%, and from about 2% to about 4% by weight of the barrier composition). In some embodiments, the active agent is present in an amount ranging from about 1% to about 3% by weight of the barrier composition 150.

Some embodiments of the barrier composition 150 as provided herein may further include an emulsifier. An emulsifier, as provided herein, includes a compound that alters the surface properties of the hydrophobic and aqueous carriers in the barrier composition 150 to aid in the formation of an emulsion. In some embodiments, an emulsifier is a surface-active agent. A surface-active agent, selected from anionic, cationic, non-ionic, zwitterionic, amphoteric, and ampholytic surfactants or combinations thereof may be used as an emulsifier. In some embodiments, an emulsifier is a sorbitan, transester, sucrose ester, polymer, silicone, fatty alcohol, stearate, glucoside, or a mixture of two or more thereof. Non-limiting examples of emulsifiers include polysorbates, such as polyoxyethylene (20) sorbitan monostearate (Tween 60) and polyoxyethylene (20) sorbitan monooleate (Tween 80); stearates such as glyceryl stearate and PEG-100 stearate; hydroxyethylacrylate/sodium acryloyldimethyl taurate copolymer; cetyl dimethicone; potassium cetyl phosphate; polyoxyethylene (POE) fatty acid esters, such as Myrj 45, Myrj 49 and Myrj 59; poly(oxyethylene) alkyl ethers, such as poly(oxyethylene) cetyl ether, poly(oxyethylene) palmityl ether, polyethylene oxide hexadecyl ether, polyethylene glycol cetyl ether, brij 38, brij 52, brij 56, and brij W1; sucrose esters; partial esters of sorbitol and sorbitol anhydrides, such as sorbitan monolaurate and sorbitan monolaurate-mono or diglycerides; isoceteth-20; sodium methyl cocoyl taurate; sodium methyl oleoyl taurate; sodium lauryl sulfate; triethanolamine lauryl sulfate; betaines; and mixtures of two or more thereof.

An emulsifier may be present in a barrier composition 150 in an amount ranging from about 0.1% to about 10% by weight of the composition. In some embodiments, an emulsifier may be present in a barrier composition 150 in an amount ranging from about 0.5% to about 10% by weight of the composition. For example, an emulsifier can be present in an amount ranging from about 0.5% to about 5% by weight of the barrier composition (e.g., from about 0.5% to about 4%, from about 0.5% to about 3%, from about 0.5% to about 2%, from about 0.5% to about 1.5%, from about 0.5% to about 1%, from about 0.75% to about 5%, from about 1% to about 5%, from about 1.5% to about 5%, from about 2% to about 5%, from about 3% to about 5%, from about 0.75% to about 2.5%, from about 1% to about 4%, from about 1.5% to about 3.5%, and from about 2% to about 4% by weight of the barrier composition).

Some embodiments of the barrier composition 150 may optionally include one or more emollients. An emollient may be included in the barrier composition 150 to soften or hydrate the skin to which the barrier composition is applied. Non-limiting examples of emollients include: isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristal myristate, triisocetyl citrate, octyl dodecanol, sucrose esters of fatty acids, octyl hydroxystearate, avena sativa (oat kernel) extract, dimethicone, cetyl dimethicone, and mixtures of two or more thereof. Other examples of other suitable emollients can also be found in the Cosmetic Bench Reference, pp. 1.19-1.22 (1996).

In particular embodiments, the barrier composition 150 can include about 1% to about 20% by weight of one or more emollients. For example, an emollient can be present in the barrier composition in an amount ranging from about 5% to about 15% of the barrier composition (e.g., from about 5% to about 12%, from about 5% to about 10%, from about 5% to about 8%, from about 6% to about 15%, from about 8% to about 15%, from about 10% to about 15%, from about 13% to about 15%, from about 6% to about 12%, from about 7% to about 11%, from about 8% to about 14%, and from about 9% to about 13% by weight of the barrier composition).

Some embodiments of the barrier composition 150 may optionally contain a pharmaceutically acceptable thickening agent and/or film former. A thickening gent increases the viscosity of the formulation so as to inhibit its spread beyond the site of application. Non-limiting examples of a thickening agent includes silica, balsam fir, hydroxyethylacrylate/sodium acryloyldimethyl taurate copolymer, and vp/hexadecene copolymer.

A film former, when it dries, forms a protective film over the site of application. The film inhibits removal of the active agent and keeps it in contact with the site of application (e.g., the targeted skin surface 50). Examples of film formers that are suitable for use in the compositions provided herein include adipic acid/diethylene glycol/glycerin crosspolymer and a copolymer of eicosene and vinyl pyrrolidone.

Various additives may be included in some embodiments of the barrier composition 150. For example, solvents, including relatively small amounts of alcohol, may be used to solubilize certain formulation components. The barrier composition 150 may also include selected additives such as opacifiers (e.g., zinc oxide, silica), antioxidants, fragrance, colorants, stabilizers, and the like.

Some embodiments of the barrier composition 150 provided herein have a pH ranging from about 5.0 to about 8.0 (e.g., about 5.5 to about 7.5, about 5.5 to about 7.0, and about 5.5 to about 6.5). In some embodiments, the pH of the barrier composition 150 can be adjusted using organic acids such as citric acid, succinic acid, or apple cider vinegar.

Accordingly, in some embodiments, the barrier composition 150 provided herein can include:
from about 30% to about 90% by weight of the composition of a vehicle,
from about 0.5% to about 5% by weight of the composition of a preservative, and
from about 0.5% to about 5% by weight of the composition of an active agent, wherein the total components add up to 100%. For example, the barrier composition 150 can include:
from about 30% to about 90% by weight of the composition of a vehicle,
from about 0.1% to about 10% by weight of the composition of an emulsifier,
from about 0.5% to about 5% by weight of the composition of a preservative, and
from about 0.5% to about 5% by weight of the composition of an active agent, wherein the total components add up to 100%. In some embodiments, a vehicle can include a hydrophobic carrier and an aqueous carrier. In such embodiments, the barrier composition 150 can include:
from about 5% to about 80% by weight of the composition of a hydrophobic carrier, from about 35% to about 80% by weight of an aqueous carrier (e.g., water), from about 0.1% to about 10% by weight of the composition of an emulsifier, from about 0.5% to about 5% by weight of the composition of a preservative, and from about 0.5% to about 5% by weight of the composition of an active agent, wherein the total components add up to 100%.

Further examples of the barrier composition 150 are provided below in Examples 1-11.

The barrier composition 150 may be produced in a form suitable for application to a targeted skin surface 50 using, for example, the various medical delivery devices described herein or other such delivery devices. For example, the barrier composition 150 may be produced in the form of a cream, lotion, solution, gel, ointment, paste, films (paints), bioadhesive, or the like, and/or may be prepared so as to contain liposomes, micelles, and/or microspheres.

Ointments are semisolid preparations that, in some embodiments of the barrier composition 150, are based on petrolatum or other petroleum derivatives. The specific ointment vehicle to be used for particular embodiments of the barrier composition 150 is one that will provide for optimum delivery of the active agents, and, preferably, will provide for other desired characteristics as well, such as emolliency or the like. As with other vehicles, an ointment base should be inert, stable, nonirritating and nonsensitizing. Ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Water-soluble ointment bases can be prepared from polyethylene glycols of varying molecular weight.

Creams are viscous liquids or semisolid emulsions, either oil-in-water or water-in-oil. In some forms of the barrier composition 150, the cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and can contain a humectant. The emulsifier in a cream formulation is generally a nonionic, anionic, cationic, or amphoteric surfactant.

Also, in some embodiments, the barrier composition 150 may be produced in a gel form. Gels are semisolid, suspension-type systems. Single-phase gels contain organic macromolecules distributed substantially uniformly throughout the carrier liquid, which may be aqueous, but can also contain an alcohol and/or an oil. Gelling agents include, for example, crosslinked acrylic acid polymers such as the "carbomer" family of polymers, e.g., carboxypolyalkylenes that may be obtained commercially under the Carbopol® trademark; hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Further, in some embodiments, the barrier composition 150 may be produced in the form of a lotion. Lotions are preparations to be applied to the skin surface without friction, and can be liquid or semiliquid preparations in which solid particles, for example, the active agent, are present in a water or alcohol base. Lotions are usually suspensions of solids, and can include a liquid oily emulsion of the oil-in-water type. Lotions can also contain suspending agents to produce better dispersions as well as compounds useful for localizing and holding the active agent in contact with the skin, e.g., methylcellulose, sodium carboxymethylcellulose, or the like.

In further embodiments, the barrier composition 150 may be produced in the form of a paste. Pastes are semisolid dosage forms in which the active agent is suspended in a suitable base. Depending on the nature of the base, pastes are divided between fatty pastes or those made from a single-phase aqueous gels. The base in a fatty paste is generally petrolatum or the like. The pastes made from single-phase aqueous gels can incorporate carboxymethylcellulose or the like as a base.

In further embodiments, the barrier composition 150 may be produced in the form of a bioadhesive. Bioadhesives are preparations that adhere to surfaces of body tissues. Polymeric bioadhesive formulations for the barrier composition 150 can be selected based upon particular bioadhesive components from, for example, Heller et al., "Biodegradable polymers as drug delivery systems", in Chasin, M. and Langer, R., eds.: Dekker, New York, pp. 121-161 (1990); and U.S. Pat. No. 6,201,065. Non-polymeric bioadhesive formulations for the barrier composition 150, which may include certain fatty acid esters, can be selected based upon particular bioadhesive components from, for example, U.S. Pat. No. 6,228,383.

Some formulations of the barrier composition 150 may also be prepared with liposomes, micelles, and microspheres. Liposomes are microscopic vesicles having a lipid wall comprising a lipid bilayer, and can be used as drug delivery systems herein as well. Generally, liposome formulations can be used with poorly soluble or insoluble pharmaceutical agents. Liposomal preparations for use herein include cationic (positively charged), anionic (negatively charged) and neutral preparations. Cationic liposomes are available and can be used in some novel formulations of the barrier composition 150. For example, N[1-2,3-dioleyloxy) propyl]-N,N,N-triethylammonium (DOTMA) liposomes are available under the tradename Lipofectin® (GIBCO BRL, Grand Island, N.Y.). Similarly, anionic and neutral liposomes are available as well and can be used in some novel formulations of the barrier composition 150. For example, anionic and neutral liposomes from Avanti Polar Lipids (Birmingham, Ala.) can be implemented in the barrier composition 150, or other anionic and neutral liposomes can be prepared using selected materials, such as phosphatidyl choline, cholesterol, phosphatidyl ethanolamine, dioleoyl-phosphatidyl choline (DOPC), dioleoylphosphatidyl glycerol (DOPG), dioleoylphosphatidyl ethanolamine (DOPE), among others. These materials can also be mixed with DOTMA in appropriate ratios. The methods for making liposomes for use in particular embodiments of the barrier composition 150 should be well understood from the description herein.

Micelles for use in some formulations of the barrier composition 150 can be comprised of surfactant molecules arranged so that their polar headgroups form an outer spherical shell, while the hydrophobic, hydrocarbon chains are oriented towards the center of the sphere, forming a core. Micelles may form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltriethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30.

The term "pharmaceutically acceptable," such as in the recitation of a "pharmaceutically acceptable carrier," is used herein to mean a compound that is not biologically or otherwise undesirable, i.e., the compound may be incorporated into a topical formulation of the invention and administered to a patient without causing any undesirable biological effects or interacting in a deleterious manner with any of the other components of the formulation in which it is contained.

The term "effective" amount or a "therapeutically effective amount" of an active agent is used herein to mean a nontoxic but sufficient amount of the drug or agent to provide the desired effect, i.e., prevention of warts by, for example, by reducing the likelihood of transmission of HPV or other microbial entities. The amount that is "effective" will vary from subject to subject, depending on the age and general condition of the individual, mode of administration, and the like. Thus, it is not always possible to specify an exact "effective amount." An appropriate "effective" amount in any individual case, however, may be determined by one of ordinary skill in the art using routine experimentation.

The term "topical administration" is used herein to mean delivery of a topical drug or pharmacologically active agent to the skin or mucosal tissue, as in, for example, the prevention or treatment of warts.

Referring now to FIG. 9, a number of different embodiments of the barrier composition 150 have been described in detail above. In some embodiments that include both an aqueous phase mixture and an oil phase mixture, a method 900 for manufacturing can include a step 910 of mixing the aqueous phase elements together to provide the aqueous phase mixture. For example, the aqueous phase elements can be combined with stirring until the mixture is homogenous. In some embodiments, the mixture can be heated during the mixing process.

In some embodiments, the method 900 can also include a step 920 of mixing the oil phase elements together to provide the oil phase mixture. For example, the oil phase elements can be combined with stirring until the mixture is homogenous. In some embodiments, the mixture can be heated during the mixing process.

The method 900 may further include a step 930 of emulsifying the oil phase mixture and the aqueous phase mixture to provide a barrier composition, such as the barrier composition 150 as described above. In some embodiments, an emulsifier can be added to either the aqueous or oil phases prior to step 930. Emulsification can occur using rapid agitation (e.g., using propeller mixing). In some embodiments, emulsification requires the use of an elevated temperature (e.g., a temperature from about 30° to 100° C.).

The method 900 for manufacturing can further include a step 940 wherein the resulting barrier composition is deposited into a storage container or an applicator device. For example, the barrier composition 150 can be packaged in a stable condition in the reservoir or other storage region of any of the aforementioned medical delivery devices (refer, for example, to FIGS. 1-7B).

EXAMPLES

Several embodiments of the barrier composition 150 have been described in detail above. The barrier composition 150 is preferably formulated to be dispensed to the targeted skin surface using a selected medical delivery device (refer, for example, to FIGS. 1-7B), depending upon a number of other factors that should be understood from the description herein. In some embodiments, the barrier composition 150 is formulated to set into a durable protective layer 155 (FIG. 2b) after application to the skin surface 50, and the barrier layer 155 may optionally a non-tacky, generally transparent coating along the skin surface 50 that does not interfere with the user's normal actions (e.g., walking, swimming, etc.) when wearing the barrier layer 155. Also, the barrier layer 155 is preferably formed with a thickness that is sufficient to provide a physical barrier between HPV and other microbial entities (passed from the floor surface 20) and the exterior of the skin surface 50. Furthermore, some formulations of the barrier composition 150 may optionally include one or more active anti-microbial agents, thereby enhancing the barrier layer 155 to include an anti-microbial effect that destroys or otherwise reduces the population of HPV or other microbial entities contacting or penetrating the barrier layer 155 or that otherwise inhibits infection from HPV or other microbial entities. A number of suitable, non-limiting examples of the barrier composition 150 are described below:

Example 1—Biphasic Formulations

The following formulae are biphasic with an oil phase dispersed in an aqueous phase. The formulations are prepared by mixing the two phases separately followed by emulsifying the oil phase in the water phase by rapid agitation during mixing at an appropriate temperature.
Formula 1
Aqueous Phase: Hydroxyethylacrylate/sodium acryloyldimethyl taurate copolymer (1%); hydrated silica (1%); Ethylhexyl glycerin (2%); dextran (3%); Glycerin (5%); Water (q.s., 52%)
Oil Phase: Monolaurin (1%); Isopropyl myristate (6%); lanolin (1%); triglyceryl diisostearate (3%); cetyl dimethicone (2%); VP/hexadecane copolymer (2%); [methylparaben; ethylparaben; isopropylparaben; isobutyl paraben; butyl paraben] (1%) mineral oil (20%)
Formula 2
Aqueous Phase: Echinacea extract (1%); disodium EDTA (1%); cetyl alcohol (1%); carrageenan (2%); hydrated silica (2%); PEG-150 distearate (2%); sorbitol (4%); water (q.s., 53%)
Oil Phase: Monolaurin (1%); bisabolol (1%); [methylparaben; ethylparaben; isopropylparaben; isobutyl paraben; butyl paraben] (1%); steareth-21 (2%); cyclosiloxane (4%) mineral oil (15%); sunflower oil (10%)
Formula 3
Aqueous Phase: Dipotassium glycrrhizate (1%); potassium cetyl phosphate (1%); sodium laureth-13 carboxylate (1%); cetyl alcohol (2%); alumina (3%); glyceryl stearate (3%); carrageenan (3%); propylene glycol (3%); water (q.s., 52%)

Oil Phase: steareth-21 (1%); [methylparaben; ethylparaben; isopropylparaben; isobutyl paraben; butyl paraben] (1%); cimetidine (2%); silicone oil (4%); benzyl alcohol (3%); vegetable oil (20%)

Formula 4

Aqueous Phase: sodium benzoate (0.25%); sodium palmitate (0.75%); hydrated silica (1%); hydroxyethylacrylate/sodium acryloyldimethyl taurate copolymer (1%); glyceryl stearate (2%); carrageenan (3%); dextran (3%); sorbitol (5%); water (q.s., 50%)

Oil Phase: dimethicone; cetyl dimethicone (1%); styrene/acrylates copolymer (1%); cimetidine (2%); Isopropyl myristate (2%); mineral oil (28%)

Formula 5

Aqueous Phase: sodium benzoate (0.5%); sodium palmitate (0.5%); PEG-100 stearate (1%); zinc oxide (1%); cetyl alcohol (2%); guar hydroxypropyltrimonium chloride (2%); sodium laureth-13 carboxylate (2%); ethoxy diglycol (5%); water (q.s., 55%) Oil Phase: Resveratrol (1%); stearoxytrimethyl silane (1%); chlorphenesin (1%); triglyceryl diisostearate (2%); lanolin (3%); dimethicone (3%); mineral oil (20%)

Formula 6

Aqueous Phase: aluminumhydroxide/stearic acid (1%); potassium cetyl phosphate (1%); hydrated silica (1%); dipotassium glycrrhizate (1%); PEG-150 distearate (2%); guar hydroxypropyltrimonium chloride (2%); zinc oxide (2%); glycerin (6%); water (55%)

Oil Phase: hydroxylated lanolin (1%); avena sativa (oak kernel extract) (1%); [methylparaben; ethylparaben; isopropylparaben; isobutyl paraben; butyl paraben] (1%); resveratrol (2%); benzyl alcohol (4%); sunflower oil (20%)

Formula 7

Aqueous Phase: disodium EDTA (1%); DMDM hydantoin (1%); xanthan gum (1%); titanium dioxide (1%); glyceryl stearate (2%); cetyl alcohol (2%); butylene glycol (2%); water (q.s., 60%)

Oil Phase: Tea tree oil (1%); cetyl dimethicone (1%); bisabolol (1%); styrene/acrylates copolymer (1%); isopropyl myristate (2%); dimethicone (3%); vegetable oil (21%)

Formula 8

Aqueous Phase: carrageenan (1%); zinc oxide (1%); stearoxytrimethyl silane (1%); PEG-100 stearate (2%); glyceryl stearate (2%); imidazolidinyl urea (1%); propylene glycol (7%); water (q.s., 47%)

Oil Phase: Tea tree oil (2%); benzyl alcohol (5%); triglyceryl diisostearate (3%); chlorphenesin (1%); mineral oil (27%)

Formula 9

Aqueous Phase: Benzalkonium chloride (BAC) (1%); potassium cetyl phosphate (1%); zinc oxide (1%); aluminumhydroxide/stearic acid (1%); glyceryl stearate (2%); dextran (3%); sorbitol (3%); butylene glycol (3%); water (q.s., 64%)

Oil Phase: cetyl dimethicone (1%); butylated hydroxytoluene (1%); synthetic beeswax (2%); phenoxyethanol/ethylhexylglycerin (2%); vegetable oil (15%)

Formula 10

Aqueous Phase: Dipotassium glycrrhizate (1%); hydroxyethylacrylate/sodium acryloyldimethyl taurate copolymer (1%); [methylparaben; ethylparaben; isopropylparaben; isobutyl paraben; butyl paraben] (1%); benzalkonium chloride (BAC) (2%); sodium laureth-13 carboxylate (2%); hydrated silica (2%); carrageenan (2%); propylene glycol (3%); water (q.s., 50%)

Oil Phase: steareth-21 (1%); cetyl dimethicone (2%); isopropyl myristate (2%); butylated hydroxytoluene (2%); dimethicone (3%); sunflower oil (26%)

Formula 11

Aqueous Phase: disodium EDTA (1%); sodium laureth-13 carboxylate (1%); PEG-150 distearate (2%); cetyl alcohol (2%); glyceryl stearate (2%); guar hydroxypropyltrimonium chloride (2%); titanium dioxide (2%); ethoxy diglycol (5%); water (q.s., 59%)

Oil Phase: Podophyllum (1%); bisabolol (1%); styrene/acrylates copolymer (1%); [methylparaben; ethylparaben; isopropylparaben; isobutyl paraben; butyl paraben] (1%); mineral oil (20%)

Formula 12

Aqueous Phase: Dipotassium glycrrhizate (1%); potassium cetyl phosphate (2%); PEG-100 stearate (2%); butylene glycol (8%); water (q.s., 50%)

Oil Phase: Thuja oil (1%); triglyceryl diisostearate (2%); stearoxytrimethyl silane (1%); dimethicone (3%); steareth-21 (1%); phenoxyethanol/ethylhexylglycerin (1%); lanolin (3%); mineral oil (25%)

Example 2—Water Resistant Lotion

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| A | Water | Q.S. to 100% |
| A | Disodium EDTA | 0.10 |
| B | Carbomer | 0.25 |
| B | Acrylates C10-30 Alykyl Acrylates Crosspolymers | 0.20 |
| B | Glycerin | 2.00 |
| C | C12-15 Alkyl Benzoate | 5.00 |
| C | Isononyl Isononanoate | 2.50 |
| C | Caprylic/Capric Triglyceride | 7.00 |
| C | Isopropyl Palmitate | 6.00 |
| C | Cetyl Alcohol | 0.75 |
| C | Stearic Acid | 1.25 |
| C | Oxidized Polyethylene | 2.25 |
| D | Triethanolamine | 0.40 |
| E | Preservative | Q.S. |

1. Add Phase A to the main tank and heat to 75-80° C. Disperse ingredients from phase B, allowing enough time between dispersion to allow the polymer to hydrate properly. Then add glycerin to Phase A while maintaining temperature.
2. In a separate tank, blend the items from Phase C (holding back Sensymer). Heat the mixture to obtain a clear phase (75-80° C. with propeller mixing) then add Sensymer and continue heating (to slightly over 95° C.) to allow Sensymer to become incorporated into the oil phase.
3. At 75-80° C., form an emulsion by adding Phase C to Phase A/B with vigorous propeller mixing, following with addition of Phase D (neutralizer). Homogenize the batch mixture at 3500 rpm, then return to propeller mixing.
4. Cool to <50° C. and add Phase E.

Appearance: white cream
pH: 5.5-6.0

Example 3—Water Resistant Lotion

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| A | Water | Q.S. to 100% |
| B | Methyl Glucose Sequistearate | 1.00 |
| B | PEG-20 Methyl Glucose Sesquistearate | 1.00 |
| B | VP/Eicosene Copolymer | 2.00 |
| B | Cetearyl Alcohol & Ceteareth-20 | 3.00 |
| B | Isopropyl Myristate | 5.00 |
| B | Caprylic/Capric Triglyceride | 9.00 |
| B | Isopropyl Palmitate | 10.00 |
| C | Preservative | Q.S. |
| D | Citric Acid | Q.S. |

1. Heat Phase A to 75-80° C.
2. In a separate container, add the Phase B components and heat to 75-80° C. until all solids have dissolved and a homogeneous phase is formed.
3. When both phases are hot, add Phase B to Phase A with mixing and homogenize until desired particle size is achieved.
4. Adjust pH with 50% citric acid solution.

Appearance: white cream
pH: 7.0-7.5

Example 4—Water Resistant Lotion

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| A | Sodium Stearoyl Glutamate | 0.70 |
| A | Pentaerythrityl Distearate | 2.00 |
| A | Dicaprylyl Carbonate | 4.00 |
| A | Dimethicone | 2.00 |
| A | Isooctyl Caprylate/Caprate | 9.00 |
| A | Isopropyl Myristate | 7.00 |
| A | Caprylic/Capric Triglyceride | 5.00 |
| A | Isopropyl Palmitate | 12.00 |
| A | Hydrogenated Dimer Dilinoleyl/Dimethylcarbonate Copolymer | 4.00 |
| A | Sodium Polyacrylate | 0.60 |
| B | Water | Q.S. to 100% |
| B | Preservative | Q.S. |

1. Combine Phase A components and heat to 75° C.
2. Combine Phase B components and heat to 75° C.
3. Add Phase B to Phase A and slowly cool the mixture to 55° C.
4. Homogenize and continue to cool to ambient temperature.

Appearance: white cream
H: 6.0-6.5
Viscosity: 170,000 cps

Example 5—Water Resistant Lotion

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| A | Caprylic/Capric Triglyceride | 9.25 |
| A | Isopropyl Palmitate | 9.25 |
| A | 2-Ethylhexyl Palmitate | 5.40 |
| A | Stearyl Alcohol | 4.50 |
| A | Ceteareth-20 | 0.50 |
| A | PEG-12 Dimethicone | 0.50 |
| A | C12-15 Alkyl Benxonate & Diproplyene Glycol Dibenzoate, PPG-15 Stearyl Ether Benzoate | 5.00 |
| B | Xanthan Gum | 0.30 |
| B | Glycerin | 5.00 |
| C | Water | Q.S. to 100% |
| C | Polyurethane-2 & Polymethyl Methacrylate | 2.50 |
| D | Preservative | Q.S. |
| | Citric Acid | Q.S. |

1. Combine Phase A and mix.
2. Premix Phase B components.
3. In main mixing vessel, add water and then slowly add Phase B premix while stirring. Continue to stir until clear homogeneous mixture forms.
4. Add Phase C components to main mixing vessel with stirring.
5. Heat both vessels to 80-85° C. Slowly add Phase A to Phase B with stirring.
6. Remove from heat and homogenize.
7. Mix and cool to <30° C. Add Phase D.
8. Adjust pH with citric acid solution Appearance: white cream
pH: 6.0-6.5
Viscosity: 6,600-7,000 cps Example 6—Water Resistant Lotion The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| A | Xanthan Gum | 0.40 |
| A | Glycerin | 2.50 |
| B | Water | Q.S. to 100% |
| B | Tetrasodium EDTA | 0.10 |
| B | Caprylyl Glycol | 1.00 |
| C | Hydroxyethylacrylate/Sodium Acryloyldimethyltaurate Copolymer & Squalane & Polysorbate 60 | 3.50 |
| D | Caprylic/Capric Triglyceride | 13.25 |
| D | Isopropyl Palmitate | 13.25 |
| D | Glyceryl Stearate & PEG-100 Stearate | 2.50 |
| D | Isooctyl Caprylate/Caprate | 2.25 |
| D | Adipic Acid/Diethylene Glycol/Glycering Crosspolymer | 3.00 |
| E | Preservative | q.s. |

1. Premix Phase A.
2. In main tank, add Phase B. With mixing, add Phase A to Phase B with mixing and mix until uniform.
3. Heat Phase AB to 75-80° C. and mix with propeller agitation until uniform.
4. Slowly add Phase C. Mix until uniform.
5. In a separate tank, combine Phase D components. Heat to 75-80° C. and mix with propeller agitation until uniform.
6. Add Phase D to Phase A/B/C and mix until uniform.
7. Homogenize at 3500 rpm.
8. Cool to 25-30° C. with mixing.

Appearance: white cream
pH: 6.0-6.5
Viscosity: 44,000 cps (spindle T-C at 10 rpm at 25 C)

Example 7—Water Resistant Spray

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| A | Alcohol Denat. | Q.S. to 100% |
| A | Water | 5.00 |
| A | Acrylates/Octylacrylamide Copolymer | 2.00 |
| B | Caprylic/Capric Triglyceride | 13.00 |
| B | Isopropyl Palmitate | 13.00 |
| B | C12-15 Alkyl Benzoate | 2.00 |
| C | Preservative | Q.S. |

1. Combine Phase A (except Dermacryl 79 polymer). Slowly sift in Dermacryl 79 polymer, and mix until uniform.
2. Combine Phase B.
3. Add Phase B to Phase A, mix until uniform.
4. Add Phase C.

Example 8—Water Resistant Spray

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
|  | Alcohol Denat. | Q.S. to 100% |
|  | Polyester-10 & Propylene Glycol Dibenzoate | 2.00 |
|  | Caprylic/Capric Triglyceride | 10.00 |
|  | Isopropyl Palmitate | 11.00 |
|  | Isopropyl Myristate | 12.50 |

1. Add ingredients in order and mix until uniform after each addition.

Example 9—Water Resistant Spray

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| A | C14-22 Alkyl Alcohol & C12-20 Alkyl Glucoside | 3.00 |
| A | Caprylic/Capric Triglyceride | 5.00 |
| A | Cetearyl Alcohol & Cocoglucoside | 1.00 |
| A | Caprylic/Capric Triglyceride | 10.00 |
| A | Isopropyl Palmitate | 10.00 |
| B | Xanthan Gum | 0.40 |
| B | Glycerin | 3.00 |
| C | Water | Q.S. to 100% |
| D | Acrylates Copolymer | 2.13 |
| D | Preservative | Q.S. |

1. Mix Phase A and heat to 75-80° C.
2. Premix Phase B.
3. Add Phase C to main mix tank. With mixing, add Phase B to Phase C and mix until uniform.
4. Heat Phase B/C to 75-80° C.
5. At 75-80° C., add Phase A to Phase B/C. Homogenize at 3,000 rpm.
6. With mixing, cool to <35° C.
7. Add Phase D to main mix tank.

Example 10—Water Resistant Stick

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
|  | Polyvinyloctadecyl Ether | 2.70 |
|  | Ceresin | 2.70 |
|  | Oxokerite | 1.80 |
|  | Paraffin | 2.15 |
|  | Hydroxystearic Acid | 1.80 |
|  | Ethyl Hexyl Hysoxystearate | 2.70 |
|  | Triethylhexyl Trimallitate |  |
|  | C30-C45 Olefin |  |
|  | VP/Hexadecene Copolymer | 5.35 |
|  | Tribehenin | 2.70 |
|  | Isopropyl Myristate | 3.60 |
|  | PPG-26/Dimer Dilinoleate Copolymer | 1.80 |
|  | Dipentaerythrityl Tetrabehenate Polyhydroxystearate | 3.60 |
|  | Isopropyl Palmitate | 13.40 |
|  | PEG-40 Castor Oil | 13.40 |
|  | Caprylic/Capric Triglyceride | 10.75 |
|  | Preservative | q.s. |

1. Combine ingredients and heat to 85° C. Mix until uniform.
2. While hot pour into mold and cool.

Example 11—Butter

The formulation can include from about 0.01% to about 6% by weight of an active agent as provided herein. For example, the formulation can contain one or more of the following: 0.1% benzalkonium chloride, 0.1% chlorphenesin, 0.6% 1,3-Bis(hydroxymethyl)-5,5-dimethylimidazolidine-2,4-dione (DMDM hydantoin), or 0.01% 3-Iodo-2-propynylbutylcarbamate (IPBC).

| Phase | INCI Name | % by weight |
|---|---|---|
| | Castor Oil | Q.S. to 100% |
| | Isopropyl Myristate | 15.00 |
| | Microcrystalline Wax | 5.00 |
| | Carnauba Wax | 2.00 |
| | Trimethylpentanediol/Adipic Acid/Glycerin Crosspolymer | 1.00 |
| | Preservative | q.s. |

1. Combine ingredients and heat to 80° C. Mix until uniform.
2. Cool to 70° C. and pour into a suitable package.

A number of embodiments of the invention have been described. Nevertheless, it will be understood that various modifications may be made without departing from the scope of the invention. Accordingly, other embodiments are within the scope of the following claims.

What is claimed is:

1. A dispenser device containing a topical skin barrier composition for dispensation to a targeted skin surface, the topical skin barrier composition consisting essentially of:
   a first component selected from the group consisting of butylated hydroxytoluene, benzalkonium chloride, methylparaben, ethylparaben, isopropylparaben, isobutylparaben, heptylparaben, benzylparaben, butylparaben, chloromethylisothiazolinone, and methylisothiazolinone;
   a second component selected from the group consisting of monolaurin, Echinacea extract, cimetidine, dextran hydrogel, resveratrol, podophyllum, tea tree oil, thuja oil, carrageenan, hydrated silica, and mixtures of two or more thereof; and
   a third component that is a combination of a hydrophobic carrier and an aqueous carrier;
   wherein the dispenser device has a reservoir containing said topical skin barrier composition, and a roller, pad or nozzle for dispensing the topical skin barrier composition to form an anti-microbial barrier coating along the targeted skin surface so as to hinder transmission of wart-causing microbial entities to the targeted skin surface.

2. The device of claim 1, wherein the second component of the topical skin barrier composition in the reservoir is an active virucidal or virostatic agent that destroys or inhibits transmission of wart-causing viruses.

3. The device of claim 1, wherein the topical skin barrier composition is configured to form an anti-microbial barrier coating along the targeted skin surface to provide both a physical barrier effect and an anti-microbial effect that each hinder transmission of wart-causing microbial entities to the targeted skin surface.

4. The device of claim 1, wherein the topical skin barrier composition is configured to form an anti-microbial barrier coating that is non-tacky and generally transparent.

5. The device of claim 1, wherein the topical skin barrier composition in the reservoir is one or more of an emollient, a thickening agent, a film form, an opacifier, and a stabilizer.

6. The device of claim 3, wherein the topical skin barrier composition in the reservoir consists essentially of:
   about 1% by weight of Echinacea extract;
   about 1% by weight disodium EDTA;
   about 1% by weight cetyl alcohol;
   about 2% by weight carrageenan;
   about 2% by weight hydrated silica;
   about 2% by weight PEG-150;
   about 4% by weight sorbitol;
   about 53% by weight water;
   about 1% by weight monolaurin;
   about 1% by weight bisabolol;
   about 1% by weight of a paraben;
   about 2% by weight steareth-21;
   about 4% by weight cyclosiloxane;
   about 15% by weight mineral oil; and
   about 10% by weight sunflower oil.

7. The device of claim 1, wherein said dispenser device is the nozzle, said nozzle being a spray nozzle having an exit port in fluid communication with the reservoir containing the topical skin barrier composition, and an actuator configured to selectively open a fluid flow path from the reservoir to the exit port of the spray nozzle during dispensation of the topical skin barrier composition from the exit port, wherein the topical skin barrier composition is configured to form the anti-microbial barrier coating along the targeted skin surface to provide both a physical barrier effect and an anti-microbial effect for hindering transmission of the wart-causing viruses to the targeted skin surface.

8. The device of claim 5, wherein the exit port of the spray nozzle outputs a stream of particulate droplets of the topical skin barrier composition that is configured to provide a substantially even coating of the anti-microbial barrier coating along the targeted skin surface.

9. The device of claim 8, wherein the exit port of the spray nozzle is configured to dispense the topical skin barrier composition at a volumetric application rate of about 2 $\mu L/cm^2$ to about 4 $\mu L/cm^2$.

10. The device of claim 9, wherein the exit port of the spray nozzle is configured to dispense the topical skin barrier composition at a volumetric application rate of about 2 $\mu L/cm^2$ in this embodiment.

11. The device of claim 10, wherein the volumetric application rate from said roller, pad or nozzle is configured to provide a layer thickness of the anti-microbial barrier coating along the targeted skin surface of about 10 microns to about 50 microns.

12. The device of claim 10, wherein the volumetric application rate from said roller, pad or nozzle is configured to provide a layer thickness of the anti-microbial barrier coating along the targeted skin surface of about 20 microns to about 30 microns.

13. The device of claim 7, wherein the reservoir also contains a propellant fluid in a gaseous state at a compressed pressure.

14. The device of claim 1, wherein said roller, pad or nozzle dispenses the topical skin barrier composition so as to provide the anti-microbial barrier coating that is substantially continuous along the targeted skin surface that hinders the transmission of human papillomavirus from an external source to the targeted skin surface.

15. The device of claim 1, wherein the topical skin barrier composition is formed as a liquid solution in the reservoir of the device.

16. The device of claim 1, wherein the topical skin barrier composition provides an anti-microbial barrier coating that maintains its effects of hindering transmission of wart-causing microbial entities to the targeted skin surface after a user walks barefoot for more than 30 minutes.

17. The device of claim 1, wherein said dispenser device is the roller, said roller being a roller applicator configured to absorb a portion of the topical skin barrier composition from the reservoir of the device and to dispense said portion of the topical skin barrier composition to the targeted skin surface.

18. The device of claim 17, wherein the roller applicator has a handle and a roller sponge applicator member is movable relative to the handle, wherein the roller sponge applicator member is configured to roll along the targeted skin surface to directly contact the targeted skin surface and dispense an anti-microbial barrier coating that is substantially even along the targeted skin surface.

19. The device of claim 1, wherein said dispenser device is the pad, said pad being a disposable applicator pad having an absorbent web of material impregnated with the topical skin barrier composition, the disposable applicator pad being defined by a peripheral shape that is contoured to match a body part corresponding to the targeted skin surface.

* * * * *